(12) United States Patent
Dahl et al.

(10) Patent No.: US 9,254,116 B2
(45) Date of Patent: Feb. 9, 2016

(54) METHODS, SYSTEMS AND APPARATUSES FOR VAN-CITTERT ZERNIKE IMAGING

(75) Inventors: Jeremy J. Dahl, Durham, NC (US); Muyinatu A. Lediju Bell, Towson, MD (US); Gregg E. Trahey, Durham, NC (US)

(73) Assignee: Duke University, Durham, NC (US)

( * ) Notice: Subject to any disclaimer, the term of this patent is extended or adjusted under 35 U.S.C. 154(b) by 173 days.

(21) Appl. No.: 13/638,996

(22) PCT Filed: Mar. 30, 2011

(86) PCT No.: PCT/US2011/030516
§ 371 (c)(1),
(2), (4) Date: Jan. 16, 2013

(87) PCT Pub. No.: WO2011/123529
PCT Pub. Date: Oct. 6, 2011

(65) Prior Publication Data
US 2013/0109971 A1    May 2, 2013

Related U.S. Application Data

(60) Provisional application No. 61/320,432, filed on Apr. 2, 2010.

(51) Int. Cl.
*A61B 8/00* (2006.01)
*A61B 8/14* (2006.01)
*A61B 8/08* (2006.01)
*G01S 7/52* (2006.01)
*G01S 15/89* (2006.01)

(52) U.S. Cl.
CPC . *A61B 8/145* (2013.01); *A61B 8/08* (2013.01); *G01S 7/52046* (2013.01); *G01S 15/8977* (2013.01)

(58) Field of Classification Search
None
See application file for complete search history.

(56) References Cited

U.S. PATENT DOCUMENTS

| 6,086,539 A | 7/2000 | Guracar et al. |
| 6,530,885 B1 | 3/2003 | Entrekin et al. |
| 2004/0133104 A1 | 7/2004 | Cohen-Bacrie et al. |
| 2005/0228279 A1 | 10/2005 | Ustuner et al. |
| 2006/0054824 A1 | 3/2006 | Federici et al. |

OTHER PUBLICATIONS

Bamber, J., et al., "B-mode Speckle Texture: The Effect of Spatial Coherence," Acoustical Imaging, vol. 24, Kluwer Academic/Plenum Press, 2000, pp. 141-146.

(Continued)

*Primary Examiner* — Unsu Jung
*Assistant Examiner* — Shahdeep Mohammed
(74) *Attorney, Agent, or Firm* — Withrow & Terranova, PLLC

(57) ABSTRACT

A method of creating an ultrasound image includes receiving a return signal from a time delayed signal emitted from a plurality of transducer elements at a target the return signal comprising a measurement at each of the plurality of transducer elements formed from a plurality of reflections off of a plurality of volume elements forming a two dimensional slice of a target, computing a Van-Cittert Zernike (VCZ) curve for each of the plurality of volume elements based upon the measured return signals and creating an short-lag spatial coherence (SLSC) image comprising a plurality of pixels each associated with one of the plurality of volume elements wherein each of the plurality of pixels comprises a value computed from a metric of the VCZ curve computed for each of the associated plurality of volume elements.

22 Claims, 16 Drawing Sheets

(56) References Cited

OTHER PUBLICATIONS

Bamber, J., et al., "Spatial Coherence and Beamformer Gain," Acoustical Imaging, vol. 24, Kluwer Academic/Plenumm Press, 2000, pp. 43-48.
Brunke, S.S., et al., "An Ultrasound Research Interface for a Clinical System," IEEE Transactions on Ultrasonics, Ferroelectrics, and Frequency Control, vol. 54, No. 1, IEEE, Jan. 2007, pp. 198-210.
Camacho, J., et al., "Phase Coherence Imaging," IEEE Transactions on Ultrasonics, Ferroelectrics and Frequency Control, vol. 56, No. 5, IEEE, May 2009, pp. 958-974.
Dahl, J.J., et al., "Adaptive imaging and spatial compounding in the presence of aberration," IEEE Transactions on Ultrasonics, Ferroelectrics and Frequency Control, vol. 52, No. 7, IEEE, Jul. 2005, pp. 1131-1144.
Dahl, J.J., et al., "Spatial and temporal aberrator stability for real-time adaptive imaging," IEEE Transactions on Ultrasonics, Ferroelectrics and Frequency Control, vol. 52, No. 9, IEEE, Sep. 2005, pp. 1504-1517.
Flax, S., et al., "Phase-aberration correction using signals from point reflectors and diffuse scatterers: basic principles," IEEE Transactions on Ultrasonics, Ferroelectrics and Frequency Control, vol. 35, No. 6, IEEE, Nov. 1988, pp. 758-767.
Geiman, B., et al., "In vivo comparison of fundamental and harmonic lateral transmit beam shapes," 2000 IEEE Ultrasonics Symposium, vol. 2, IEEE, Oct. 2000, pp. 1669-1675.
Goodman, J.W., "Statistical Optics," (book) Wiley-Interscience, John Wiley & Sons, Inc., 2000, 567 pages.
Hollman, K.W., et al., "Coherence factor of speckle from a multi-row probe," Proceedings of the 1999 IEEE Ultrasoncis Symposium, vol. 2, IEEE, Oct. 1999, pp. 1257-1260.
Jensen, J.A., et al., "Calculation of pressure fields from arbitrarily shaped, apodized, and excited ultrasoundtransducers," IEEE Transactions on Ultrasonics, Ferroelectrics, and Frequency Control, vol. 39, No. 2, IEEE, Mar. 1992, pp. 262-267.
Jensen, J. A., et al., "Field: A program for simulating ultrasound systems," 10th Nordic—Baltic Conference on Biomedical Imaging, Biological Engineering and Computing, vol. 34, Supplement 1, Part 1, 1996, pp. 351-353.
Krishnan, S., et al., "Adaptive compensation of phase and magnitude aberrations," IEEE Transactions on Ultrasonics, Ferroelectrics and Frequency Control, vol. 43, No. 1, IEEE, Jan. 1996, pp. 44-55.
Li, P. et al "Adaptive imaging using the generalized coherence factor," IEEE Transactions on Ultrasonics, Ferroelectrics, and Frequency Control, vol. 50 No. 2, IEEE, Feb. 2003, pp. 128-141.
Liu, D., et al., "About the application of the van Cittert-Zernike theorem in ultrasonic imaging," IEEE Transactions on Ultrasonics, Ferroelectrics and Frequency Control, Jul. 1995, pp. 590-601, vol. 42, No. 4.
Mallart, R., et al., "Adaptive focusing in scattering media through sound-speed inhomogeneities: The van CittertZernike approach and focusing criterion," The Journal of the Acoustical Society of America, Dec. 1994, pp. 3721-3732, vol. 96, No. 6.
Mallart, R., et al., "The van Cittert-Zernike theorem in pulse echo measurements," The Journal of the Acoustical Society of America, Nov. 1991, pp. 2718-2727, vol. 90, No. 5.
Masoy, S., "Estimation and correction of aberration in medical ultrasound imaging," Doctoral thesis, Norwegian University of Science and Technology, Oct. 2004, 136 pages, http://folk.ntnu.no/sveinmas/filer/avhandling_web.pdf.
O'Donnell, M., et al., "Phase-aberration correction using signals from point reflectors and diffuse scatterers: measurements," IEEE Transactions on Ultrasonics, Ferroelectrics and Frequency Control, vol. 35, No. 6, IEEE, Nov. 1988, pp. 768-774.
Walker, W., et al., "Speckle coherence and implications for adaptive imaging," Journal of the Acoustical Society of America, Apr. 1997, pp. 1847-1858, vol. 101, No. 4.
Walker, W., et al., "The Application of K-space in Pulse Echo Ultrasound," IEEE Transactions on Ultrasonics, Ferroelectrics and Frequency Control, May 1998, pp. 541-558, vol. 45, No. 3.
International Search Report and Written Opinion for International Patent Application PCT/US2011/030516 mailed Jun. 2, 2011, 9 pages.
International Preliminary Report on Patentability for International Patent Application PCT/US2011/030516 mailed Oct. 11, 2012, 8 pages.

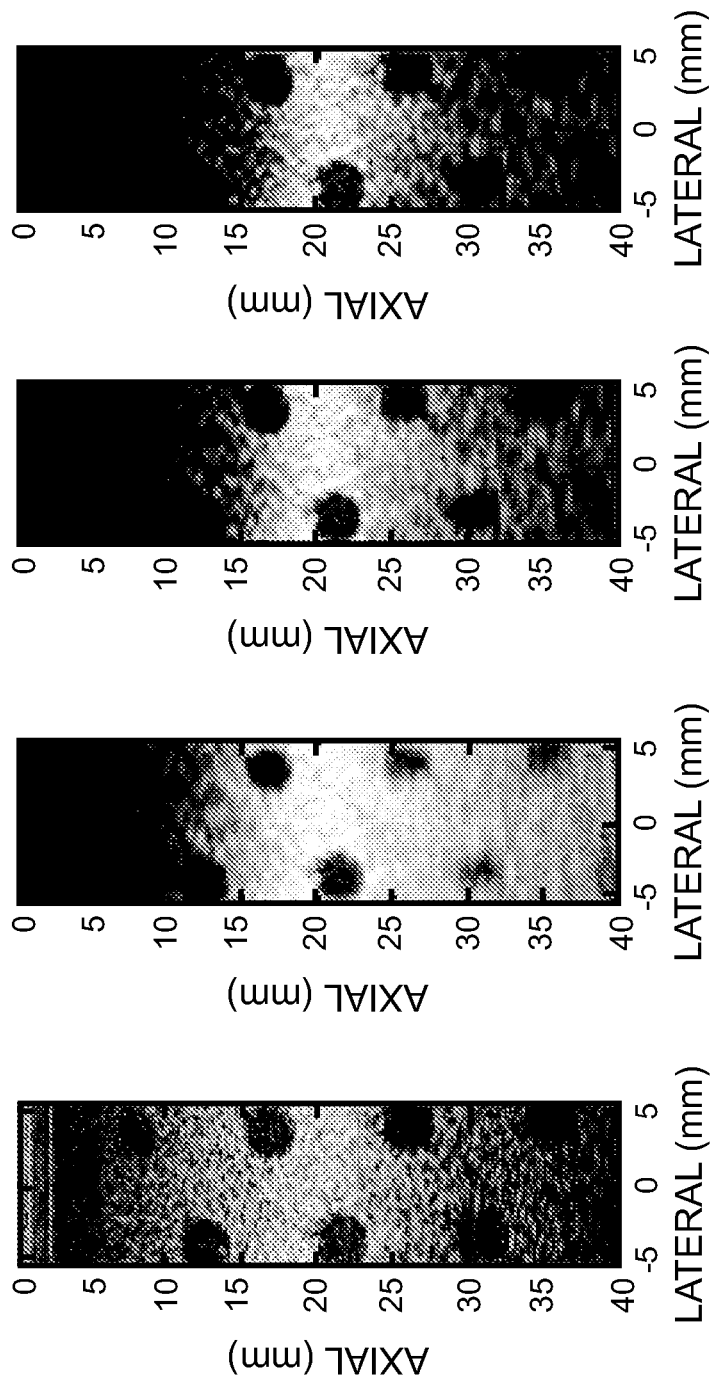

METHODS, SYSTEMS AND APPARATUSES FOR VAN-CITTERT ZERNIKE IMAGING

PRIORITY APPLICATION

This application is a 35 USC 371 National Phase filing of International Application No. PCT/US2011/30516, entitled "Methods, Systems and Apparatuses for Van-Cittert Zernike Imaging," filed Mar. 30, 2011, which claims the benefit of U.S. Provisional Patent application Ser. No. 61/320,432, entitled "Methods and Apparatus for Van-Cittert Zernike Imaging", filed Apr. 2, 2010, the disclosures of which are hereby incorporated herein by reference in their entireties.

GOVERNMENT LICENSE RIGHTS

This disclosure was made with U.S. Government support under grant numbers R21-EB008481 and R01-CA114093 awarded by the NIH National Institute of Biomedical Imaging and Bioengineering. Thus, the U.S. Government has certain rights in this invention.

FIELD OF THE DISCLOSURE

The present disclosure relates to methods, apparatuses and systems for utilizing one or more metrics derived from computing a plurality of Van-Cittert Zernike curves to produce an image.

BACKGROUND

FIG. 1 is an illustration of a differential volume element 14 in a target 16 being imaged using a B-mode ultrasound imaging technique. A transducer 10 emits a pulse, such as a pulse signal, for example, from each of a linear array of transducer elements 12(1-N) with each emitted pulse delayed by a predetermined amount. Depending on the delay utilized, an acoustic beam of energy can be aimed in a direction θ and focused onto a target 16. When the acoustic energy is reflected, such as results from a change in impedance in the target 16, some of the acoustic energy is reflected back to the transducer elements 12. By measuring the time between emitting and receiving the pulse at each of the various transducer elements 12, an amplitude of the echo such as from volume element 14 can be calculated.

By controlling the delays for a plurality of pulses, a two dimensional slice of the target may be imaged by scanning radially back and forth across a plane extending outward from the transducer 10. Such scanning, referred to as B-mode scanning, returns a reflectance value for a range of distances r across an angle Ω. When the reflectance value for all points in the plane corresponding to a distance r at an angle Ω are translated into planar coordinates, such as along the illustrated orthogonal axes X and Y, for example, an image is formed of pixels having an X and Y coordinate with the value of each pixel related to an amplitude of the echo received from a corresponding differential volume element 14 of the target 16.

Typically, the images formed from B-mode ultrasound imaging are grayscale images, where the brightness of each pixel is proportional to the magnitude of the echo received from the corresponding point in the imaged target. Because tissue is comprised of different features having different densities or compressibilities, ultrasound images of human tissue can be interpreted to determine the relative and absolute location and the acoustic reflectivity of different tissue types such as bone, soft tissue, tendons, and the like. While useful for many applications, traditional ultrasound images based upon the magnitude of a reflected signal are often times not of sufficient clarity to permit robust analysis.

It would be advantageous to generate a metric from traditional ultrasound emitted and received pulses that provides additional information regarding the nature of a target 16.

SUMMARY OF THE DETAILED DESCRIPTION

In accordance with an exemplary and non-limiting embodiment, methods, systems and apparatuses for creating an enhanced ultrasound image are provided. In one embodiment, a method of creating an ultrasound image is provided. The method comprises emitting a signal from a plurality of transducer elements at a target. The method further includes measuring a return signal at each of the plurality of transducer elements formed from a plurality of reflections off of a plurality of volume elements forming a two dimensional slice of the target. A VCZ curve for each of the plurality of volume elements is computed or otherwise determined based upon the measured return signals, and an image is created comprising a plurality of pixels each associated with one of the plurality of volume elements wherein each of the plurality of pixels comprises a value computed from a metric of the VCZ curve computed for the associated volume element. In this manner, the morphology of a wide array of biological targets may be imaged and displayed to reveal previously indiscernible features.

In another embodiment, a non-transitory computer-readable medium, comprises instructions for instructing a computer to receive a return signal from a time delayed signal emitted from a plurality of transducer elements at a target. The return signal comprises a measurement at each of the plurality of transducer elements formed from a plurality of reflections off of a plurality of volume elements forming a two dimensional slice of a target. A Van-Cittert Zernike (VCZ) curve is computed for each of the plurality of volume elements based upon the measured return signals and a short-lag spatial coherence (SLSC) image is created comprising a plurality of pixels each associated with one of the plurality of volume elements wherein each of the plurality of pixels comprises a value computed from a metric of the VCZ curve computed for each of the associated plurality of volume elements.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

Figure 9A:
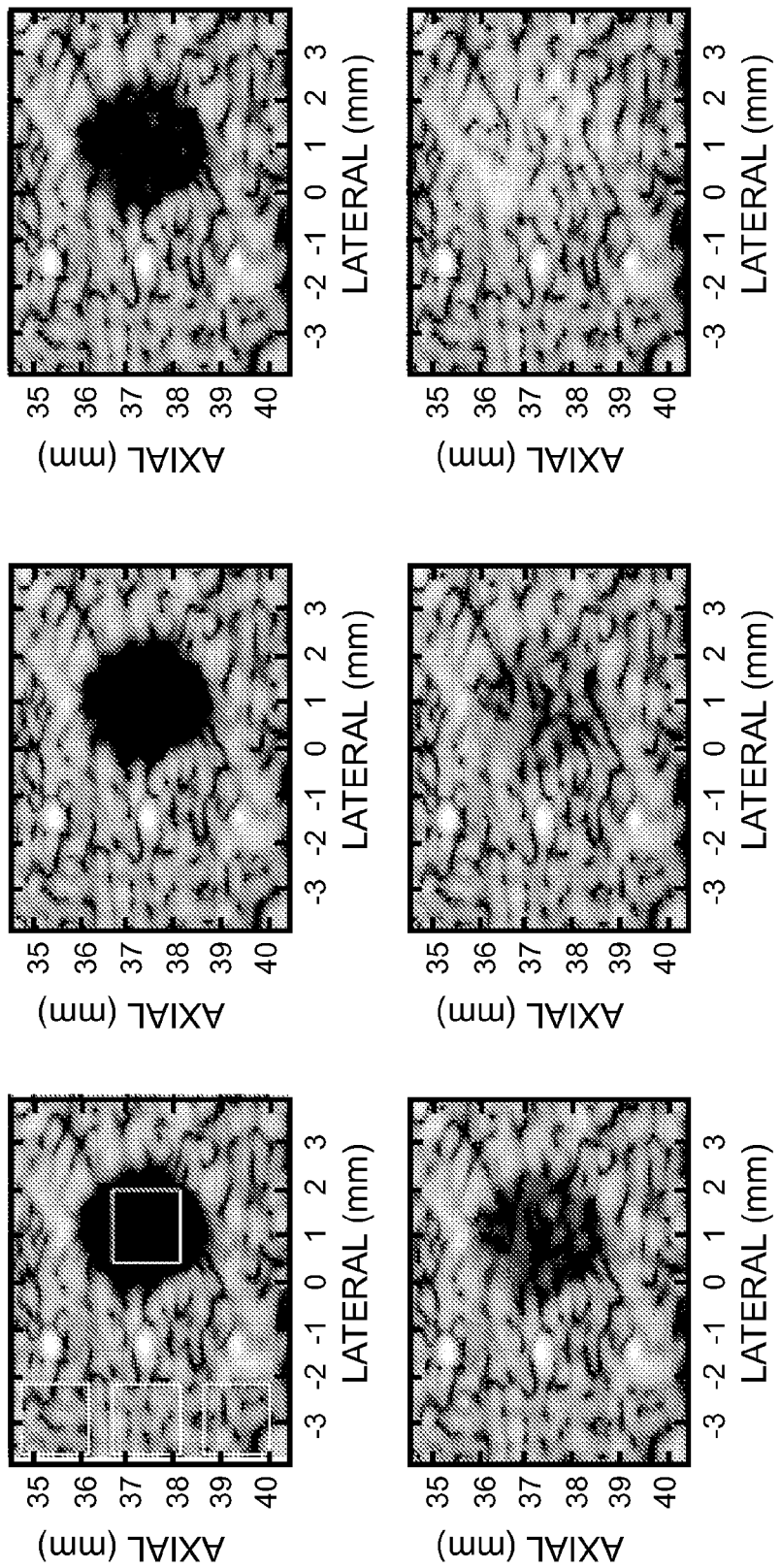
Figure 9B:
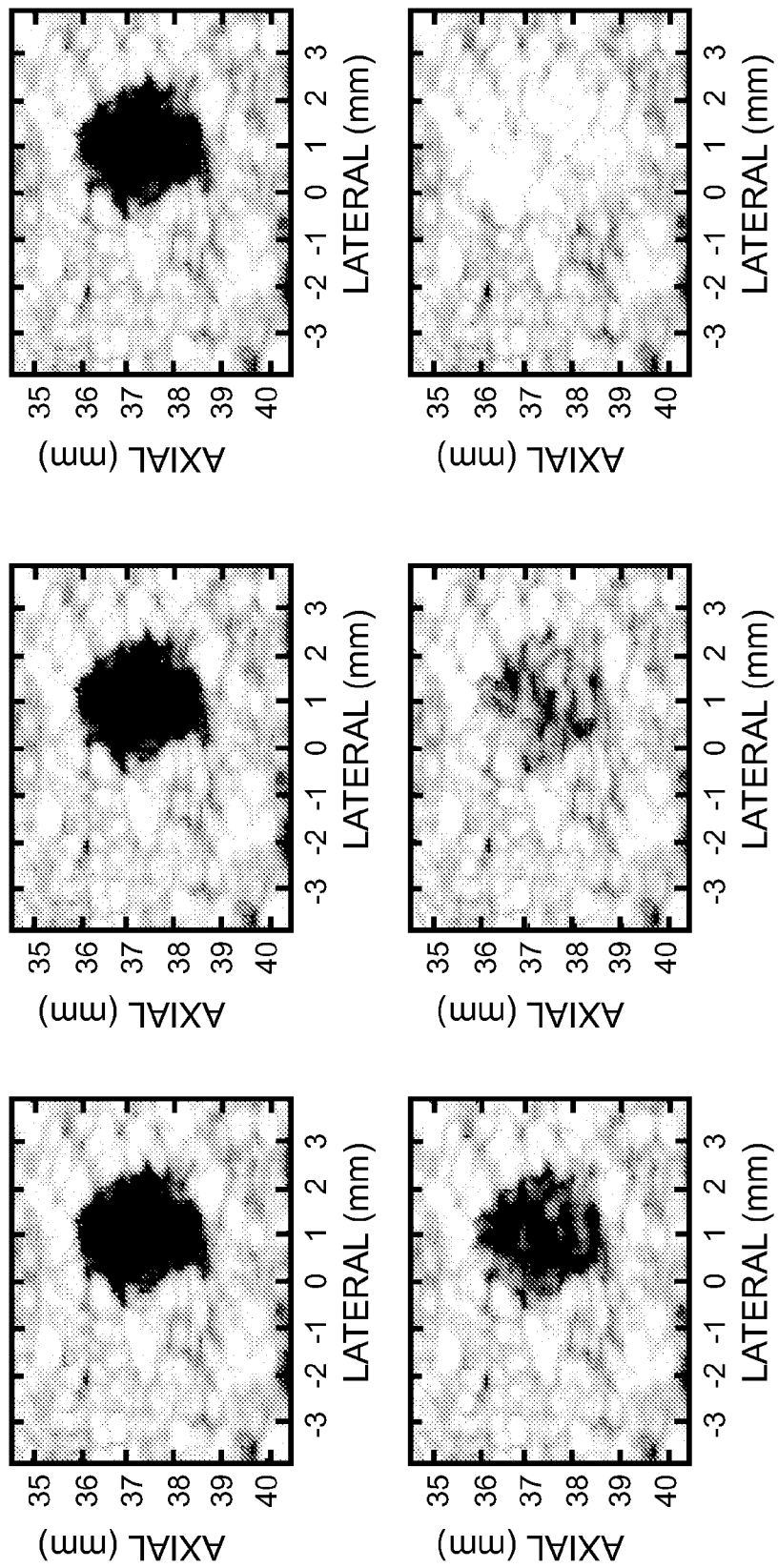
Figure 10:
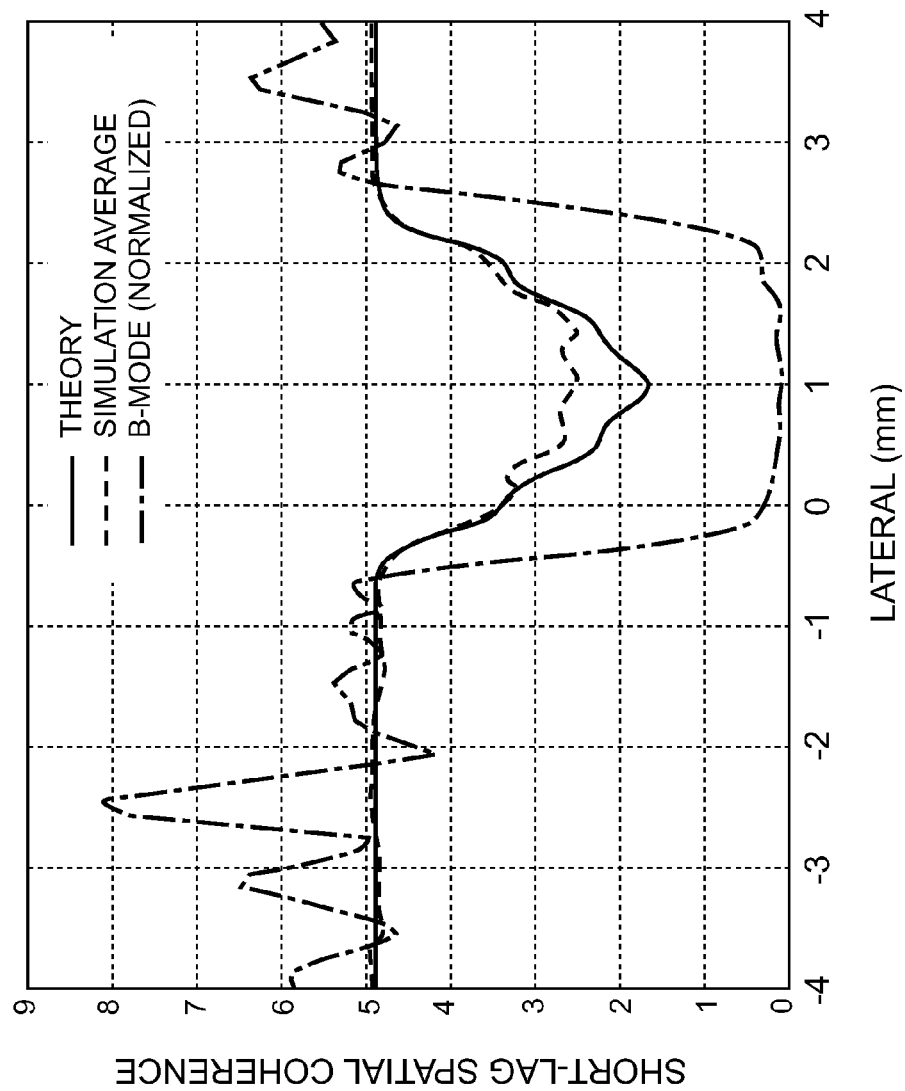
Figure 11B:
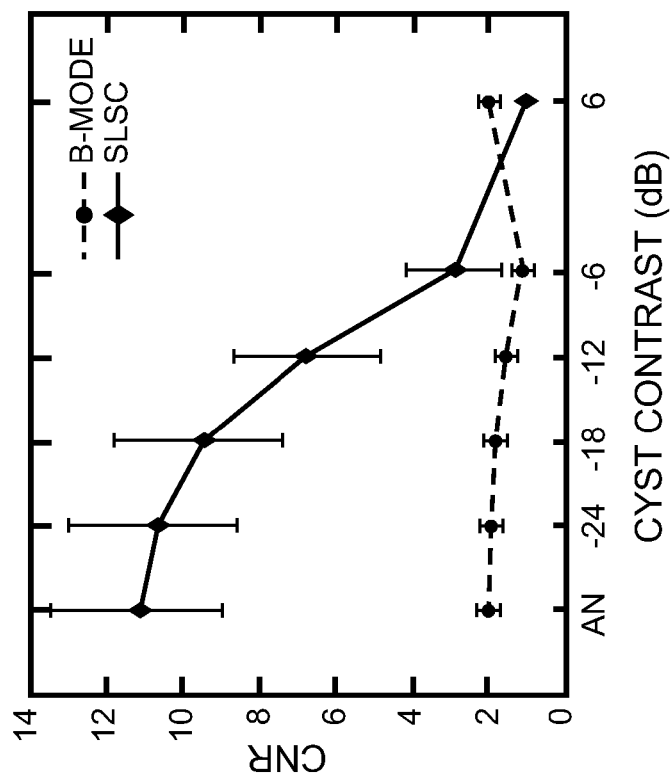
Figure 11A:
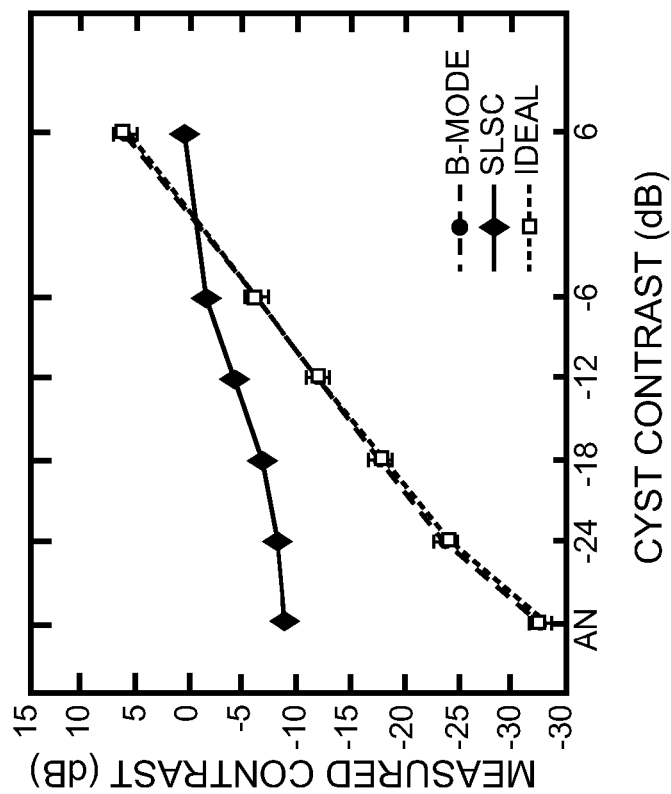
Figure 12:
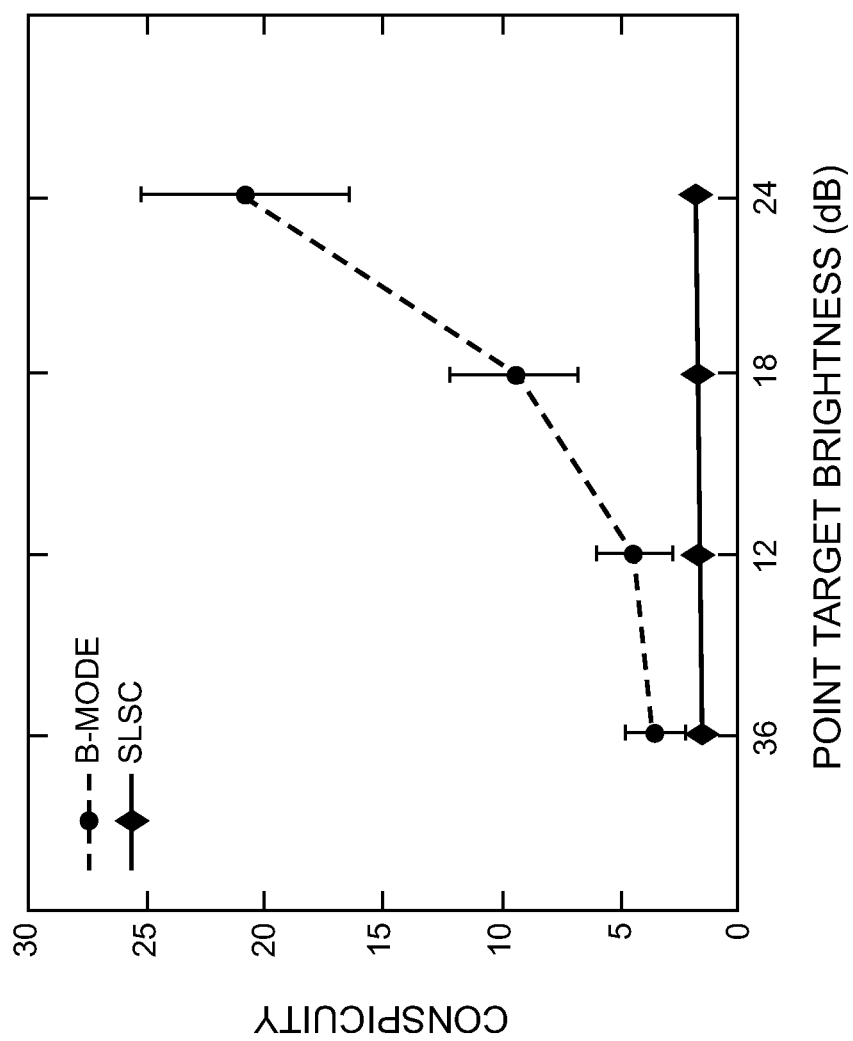
Figure 13B:
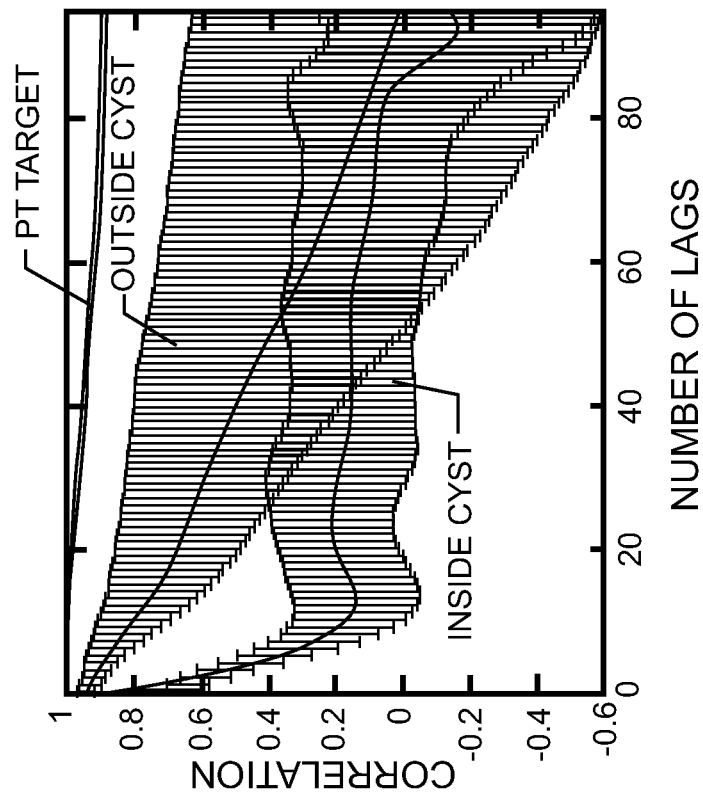
Figure 13A:
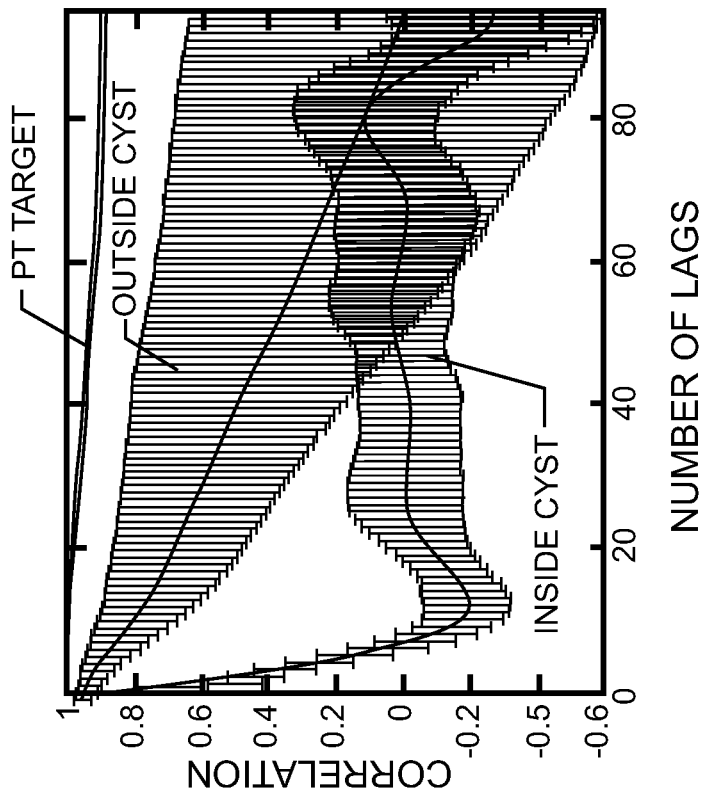
Figure 14B:
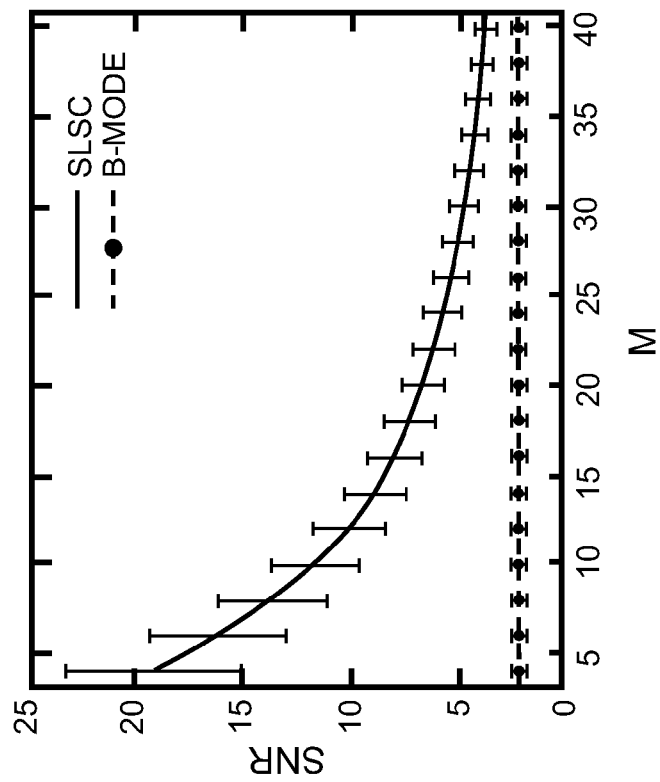
Figure 14A:
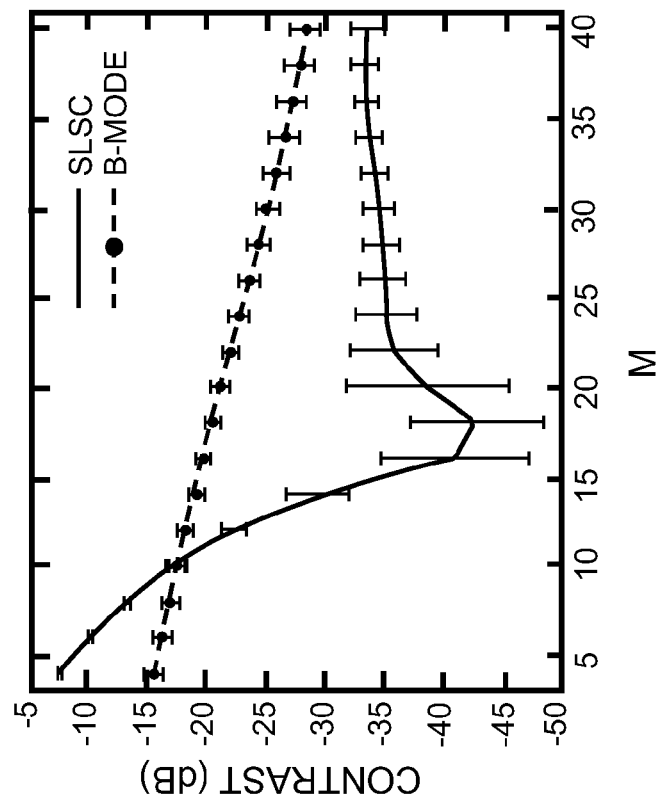
Figure 16C:
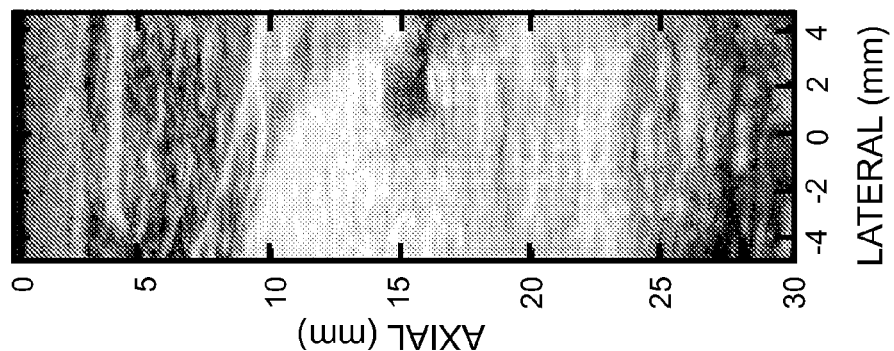
Figure 16B:
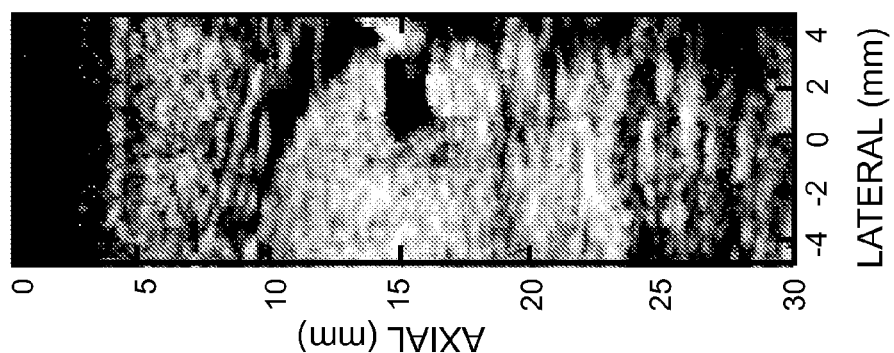
Figure 16A:
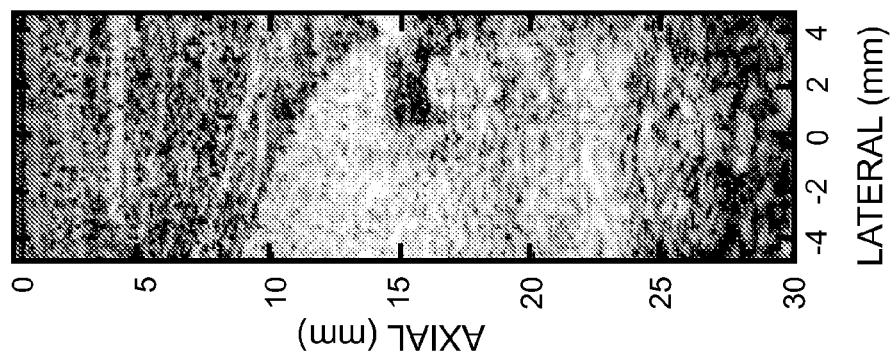
Figure 17:
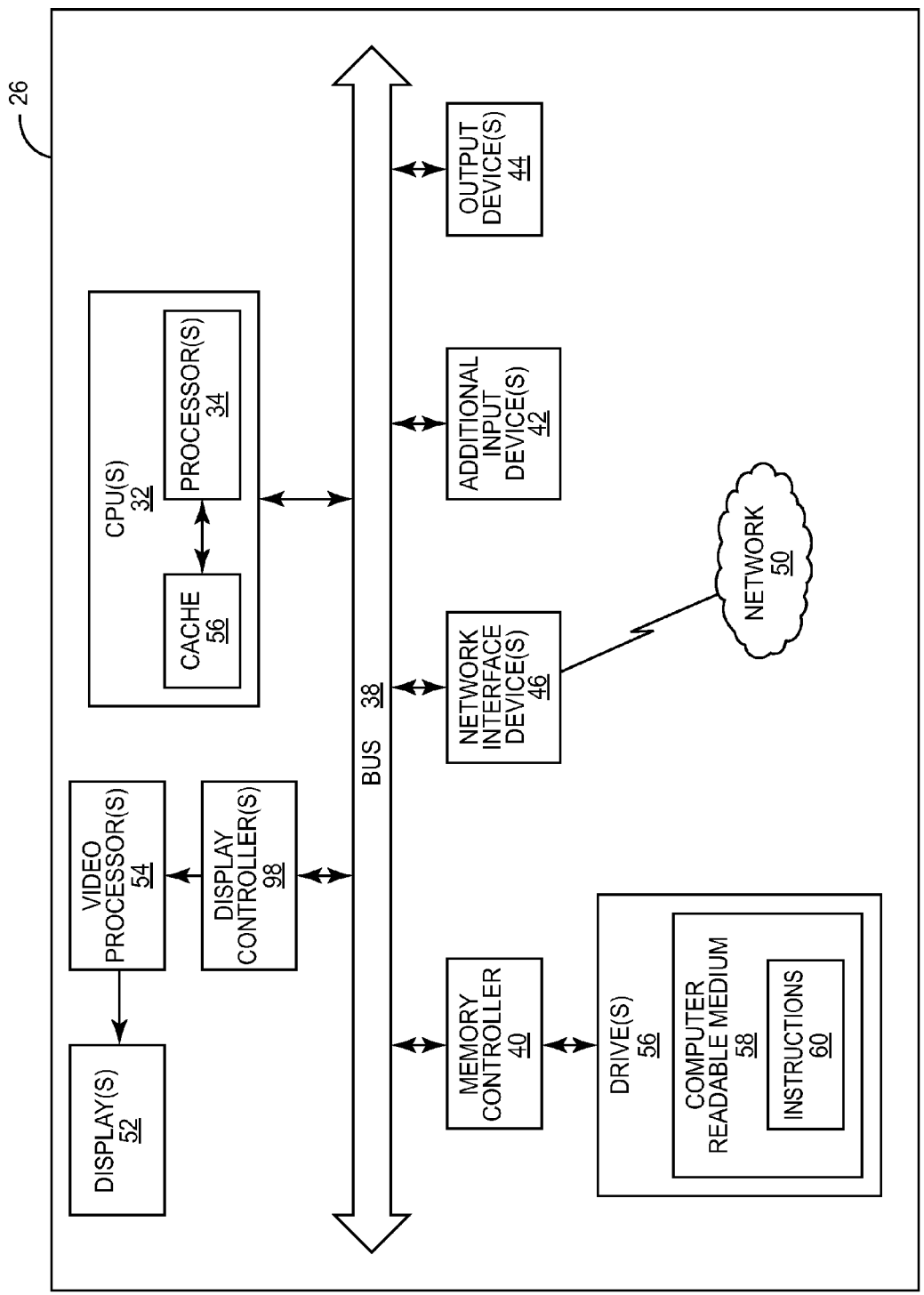

FIGS. 9A-9B are illustrations of Field II simulated B-mode and SLSC images. The B-mode images are shown with 50 dB of dynamic range and lesion contrasts of anechoic, −24 dB, −18 dB from left to right, respectively, in the first row, and −12, −6, and 6 dB from left to right, respectively, in the second row of FIG. 9A while the corresponding short-lag spatial coherence (SLSC) images are shown in rows 1 and 2 of FIG. 9B. The boxes in the first image indicate the ROIs used to calculate the contrast, CNR, SNR, and point target conspicuity according to an exemplary embodiment disclosed herein;

FIG. 10 is an illustration of a theoretical calculation of the short-lag spatial coherence image compared to the simulated B-mode and SLSC images for a lateral slice through the center of a spherical anechoic lesion according to an exemplary embodiment disclosed herein;

FIGS. 11A and 11B are illustrations of mean contrast and CNR observed in the lesions of the simulated B-mode and SLSC images according to an exemplary embodiment disclosed herein, as a function of lesion contrast wherein the error bars indicate one standard deviation;

FIG. 12 is an illustration of point target conspicuity as a function of target brightness wherein error bars indicate one standard deviation;

FIGS. 13A and 13B are illustrative demonstrations of coherence inside and outside (a) anechoic and (b) −12 dB contrast lesions in the Field II simulation wherein error bars show one standard deviation of coherence functions over the ROI;

FIG. 14A illustrates contrast and FIG. 14B illustrates SNR as a function of M wherein M indicates the maximum number of lags in Eq. 3 for the SLSC images and number of elements in the aperture for the B-mode images;

FIGS. 15A-15D illustrate B-mode (FIG. 15A) and SLSC (FIGS. 15B-15D) images of 4 mm spherical lesions in a tissue-mimicking phantom wherein the SLSC images were created with M equal to 5, 10, and 15, from left to right, respectively according to an exemplary embodiment disclosed herein;

FIGS. 16A-16C illustrate In vivo B-mode (FIG. 16A), SLSC (FIG. 15B), and spatially-compounded images (FIG. 16C) of a human thyroid wherein a cyst is visible in the thyroid at 1.5 cm depth according to an exemplary embodiment disclosed herein; and FIG. 17 is a diagram of a cross-correlation computer in accordance with an exemplary embodiment.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

In accordance with an exemplary and non-limiting embodiment, methods, systems and apparatuses for creating an enhanced ultrasound image are provided. In one embodiment, a method of creating an ultrasound image is provided. The method comprises emitting a signal from a plurality of transducer elements at a target. The method further includes measuring a return signal at each of the plurality of transducer elements formed from a plurality of reflections off of a plurality of volume elements forming a two dimensional slice of the target. A VCZ curve for each of the plurality of volume elements is computed or otherwise determined based upon the measured return signals, and an image is created comprising a plurality of pixels each associated with one of the plurality of volume elements wherein each of the plurality of pixels comprises a value computed from a metric of the VCZ curve computed for the associated volume element. In this manner, the morphology of a wide array of biological targets may be imaged and displayed to reveal previously indiscernible features.

Figure 1:
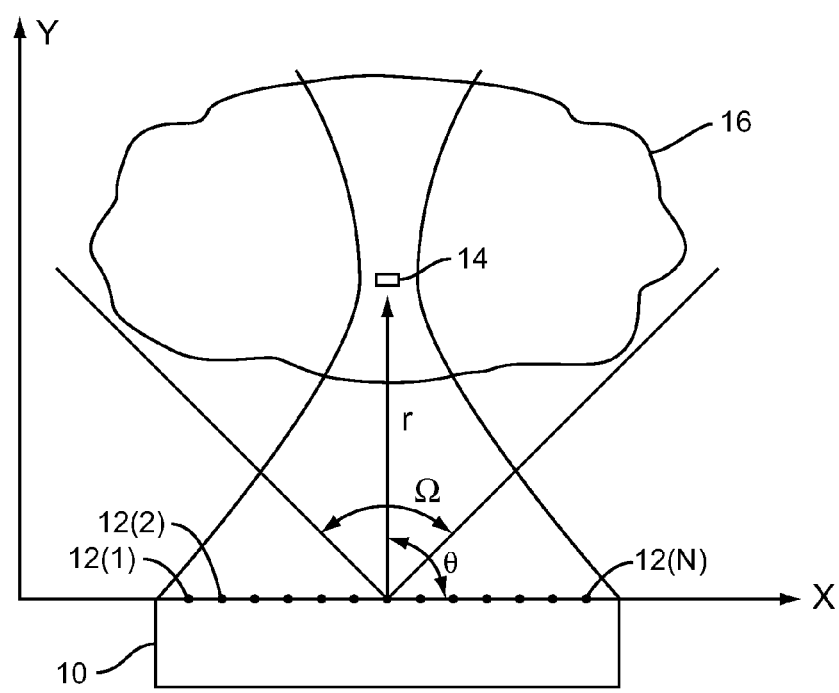
FIG. 1 illustrates a setup for practicing ultrasonic imaging.
Figure 2:
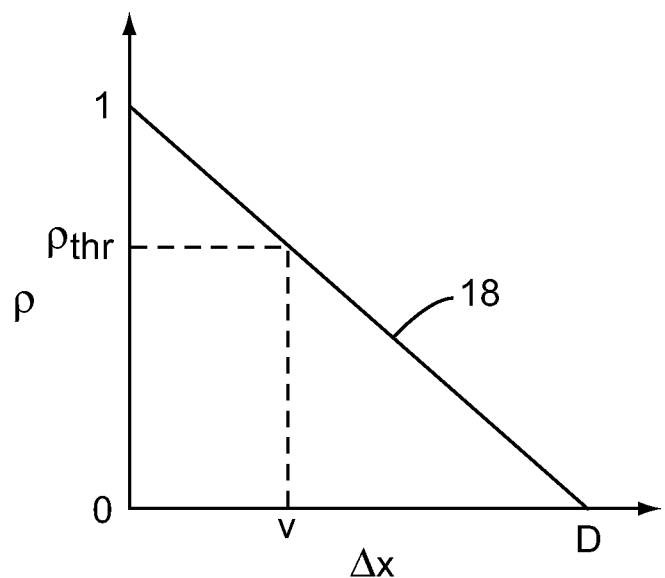
FIG. 2 is an exemplary diagram of an idealized Van-Cittert Zernike (VCZ) curve from a region of diffuse scatterers.

FIG. 2 is an illustration of a Van-Cittert Zernike (VCZ) curve, commonly referred to as a spatial coherence function, predicted by the VCZ theorem. Simply put, the VCZ theorem describes the spatial coherence of the wave that propagates from a spatially incoherent source. The spatial coherence function (or VCZ curve) is used in embodiments herein to create ultrasound images based on a plurality of metrics that can be derived from a VCZ curve, rather than relying on the simple magnitude of reflection value used in traditional B-mode imaging. As is discussed more fully below, a metric of the VCZ curve, called the short-lag spatial coherence (SLSC), may be utilized to perform VCZ imaging. As used herein, "SLSC image" refers to an image that results, in whole or in part, from such imaging.

When performing VCZ imaging as described below, the spatially incoherent source is insonified by the same plurality of linearly aligned or curvilinear transducers elements 12(1-N) each emitting delayed pulses typically utilized when performing traditional ultrasound B-mode imaging.

In traditional B-mode imaging, described above, a single brightness value, corresponding to a magnitude of a signal reflectance from a single first volume, is used to form an image. Normally such images are displayed in grayscale with the brightness of each pixel corresponding to a relative magnitude of the measured reflectance. This use of a single metric, namely, reflectance magnitude, restricts the utility of such images.

In contrast, VCZ imaging may produce numerous different images each one derived from a different characteristic, or metric, of a VCZ curve computed specifically for each pixel in the resulting SLSC image. For example, the area under a VCZ curve 18 from 0 to a given lag distance 'd' can be computed for each pixel and used to produce a SLSC image. Regardless of the metric chosen, each metric results in an SLSC image having different characteristics. As a result, the multitude of possible SLSC images that can be computed from the same data allows one to view a target in a number of different ways.

As illustrated, VCZ curve 18 is an idealized curve as might be obtained from a target 16 exhibiting uniform scattering everywhere. $\Delta x$ is the distance between two elements between which is measured a signal coherence. When the two points are coincident (i.e., a $\Delta x$ of zero), the coherence coefficient $\rho$ is one (1). Conversely, when the two points are maximally separated (i.e., a $\Delta x$ equal to the transmit aperture, D), the coherence coefficient $\rho$ is, on average, zero (0). For intermediate distances, the coherence coefficient $\rho$ tends to decrease as $\Delta x$ increases.

Note that, once a VCZ curve is computed, various metrics may be derived. For example, for a given threshold value of the coherence coefficient $\rho_{thr}$, a width of the VCZ curve 18, v, can be computed.

Figure 3:
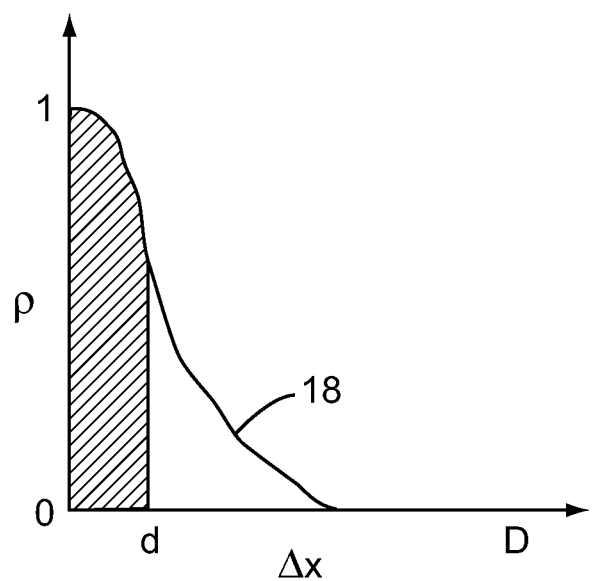
FIG. 3 is a diagram of an Van-Cittert Zernike (VCZ) curve according to an exemplary embodiment disclosed herein.

FIG. 3 is an illustration of an exemplary VCZ curve 18 computed at a point in a target from a B-mode transducer having, for example, twenty-one (21) emitting elements 12(1)-12(21) each element separated from its neighboring elements by a unit $x_1$. In this example, the target is formed such that there is not experienced uniform scattering at every point in the target. The distance between any two elements 12, $\Delta x$, is therefore an integer multiple of $x_1$. For example, the distance, or difference in position, between element 12(2) and element 12(5) is a $\Delta x$ of three (3). This distance is referred to as the lag distance 'd'. Similarly, the lag distance d between element 12(7) and element 12(10) is also three (3). The number of element 12 combinations having the same lag distance d varies for any given number of elements 12.

In the present example, wherein there are twenty-one (21) elements 12, there are, for example, eighteen (18) combination of elements 12 having a lag distance d equal to three (3). Specifically, the following combinations of elements 12 have a lag distance of three (3): element 12(1) and element 12(4), element 12(2) and element 12(5), element 12(3) and element 12(6), element 12(4) and element 12(7), element 12(5) and element 12(8), element 12(6) and element 12(9), element 12(7) and element 12(10), element 12(8) and element 12(11), element 12(9) and element 12(12), element 12(10) and element 12(13), element 12(11) and element 12(14), element 12(12) and element 12(15), element 12(13) and element 12(16), element 12(14) and element 12(17), element 12(15) and element 12(18), element 12(16) and element 12(19), element 12(17) and element 12(20), and element 12(18) and element 12(21). As is evident, the number of element 12 combinations having a given lag distance d is equal to NumElements–'d', where Num Elements is the total number of elements 12. In the present example, NumElements is equal to twenty-one (21).

Note that the number of element 12 combinations having a given lag distance d decreases as the lag distance d increases such that when the lag distance d is at a maximum, there is only one (1) element 12 combination. For example, in the present example, there is only one element 12 combination, specifically, element 12(1) and element 12(21) having a lag distance of twenty (20). As before, with reference to FIG. 2, when the lag distance d is equal to zero (0) (i.e., the coherence function is computed for a single element 12), the coherence coefficient $\rho$ is equal to one (1). Note that, when the target does not exhibit uniform scattering at each point within the target, the VCZ curve 18 differs from the idealized VCZ curve 18 of FIG. 2. Specifically, the slope of the VCZ curve 18 changes as $\Delta x$ increases from zero (0) to D.

In an exemplary embodiment, the coherence coefficient $\rho$ for each lag distance d is computed as the average of coherence coefficients $\rho$ measured for each transducer element 12 pair having a lag distance of d. For example, as illustrated above, the correlation coefficients $\rho$ for each of seventeen (17) transducer element 12 pairs may be averaged to obtain the coherence coefficient $\rho$ of the VCZ curve 10 at $\Delta x$ equal to four (4).

Note that for each volume element 14 in a target, the strength of a pulse received at each of a plurality of transducer elements 12 can be measured and a VCZ curve 10 computed. As each volume element corresponds to a pixel in an image, each pixel may be assigned a value derived from a metric of the VCZ curve 10. As used herein, "VCZ imaging" refers to creating an image wherein a value for each pixel in the image corresponds to an attribute or metric of a VCZ curve measured at a volume element corresponding to the pixel.

In traditional B-mode imaging, described above, a single intensity value, corresponding to a signal reflectance from a single point, is used to form an image. Normally such images are displayed in gray scale with the magnitude of each pixel corresponding to a relative intensity of the measured reflectance. In contrast, VCZ imaging may produce numerous different images each one derived from a different characteristic, or metric, of a VCZ curve computed specifically for each pixel in the resulting SLSC image. For example, the area under a VCZ curve 18 at a given lag distance d can be computed for each pixel and used to produce an SLSC image.

Figure 4:
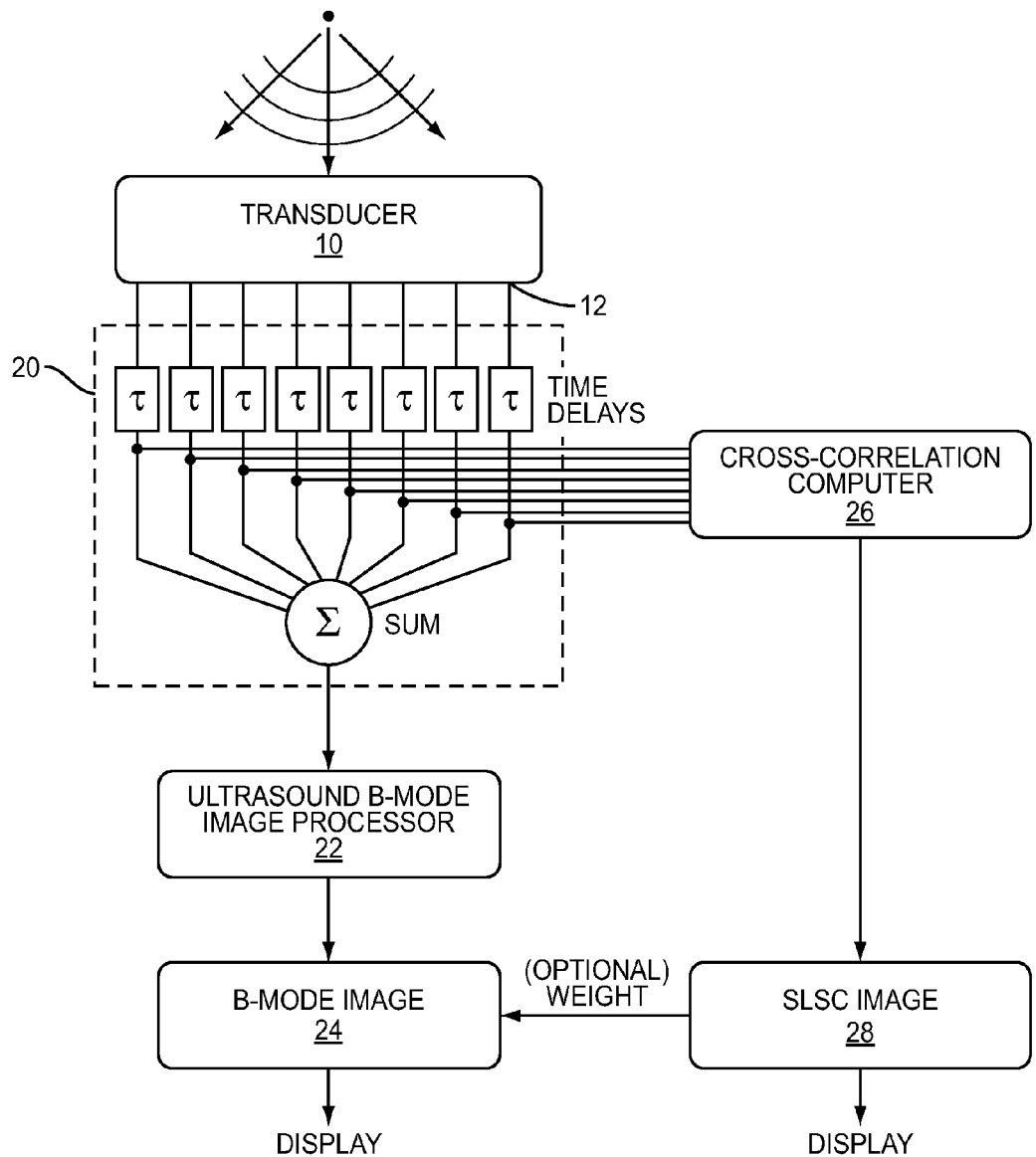
FIG. 4 is a functional apparatus diagram of an exemplary embodiment of imaging disclosed herein.

FIG. 4 is an illustration of the relationship of VCZ imaging to B-mode imaging. As illustrated, a transducer 10 emits a signal from a plurality of transducer elements 12(1-N). A beamformer 20 applies a plurality of delays to the signal and emits each delayed signal from one of the transducer elements 12. The return echoes from the transmitted signals are measured by the transducer elements 12, summed, and passed to an ultrasound B-mode image processor 22 where the measured return signals are used to create a two dimensional B-mode image 24.

In accordance with exemplary embodiment disclosed above, the measured return signals at each of transducer elements 12 may also be used, such as by a cross-correlation computer 26, prior to summing, to compute a plurality of cross-correlations from which may be derived a VCZ curve 18 at each volume element 14 in a target located upon a plane. Cross-correlation computer 26 may be implemented in hardware, software, or any combination thereof. In accordance with other exemplary and non-limiting embodiments, various spatial coherence estimation techniques may be employed including, but not limited to, Sum of Absolute Differences, Kasai's 1-D autocorrelators, and Loupas' 2-D autocorrelators. The Kasai and Loupas autocorrelators are phase-shift estimation techniques often employed in Doppler imaging. They estimate the phase difference between two signals. However this phase difference can be used as some form of estimate of the spatial coherence function.

Next, one or more metrics of the VCZ curve 18 computed at each volume element (e.g., area, slope, width, etc.) is selected to form a value for each of a plurality of pixels each corresponding to a volume element 14 in the target to create a SLSC image 28. The resulting SLSC image 28 may then be displayed.

In an exemplary embodiment, the selected VCZ curve 18 metric may also be used to enhance a B-mode image. In one exemplary embodiment, the values of the pixels in a SLSC image 28 may be combined with the corresponding pixel values in a B-mode image 24. As described more fully below, the SLSC image 28 pixel values may be weighted prior to combination with the B-mode image.

As described above, the normal computation of the VCZ curve 10 involves the correlation between all transducer element 12 pairs in the aperture of a transducer. Transducer element 12 pairs that are separated by the same lag or angle relative to the reflecting volume element 14 of a target 16 are averaged together. Therefore, each sample in the VCZ curve 18 has some associated variance. This variance of the VCZ curve 18 samples is another metric that can be used to create SLSC images. Additional algorithms, components, applications, and methods derived from or related to the use of a VCZ curve 18 to perform VCZ imaging are described more fully below.

VCZ imaging may be utilized to suppress clutter and increase imaging contrast. For example, in locations where a target medium may be hypoechoic (e.g., blood vessels, heart chambers, etc), signals returned to transducer elements 12 from such regions may be predominantly noise. Thus, the VCZ curve 18 indicates low coherence across the aperture and the VCZ curve 18 rolls off sharply. In tissue without clutter, the VCZ curve 18 indicates coherence across the aperture, and the VCZ curve 18 should roll off slowly, or in the ideal case illustrated in FIG. 2, be a straight line. Thus, the SLSC image 18 will show high contrast for anechoic/tissue regions.

In low contrast tissue targets, or tissue that exhibits overlying clutter, the variance or other metric computations applied to the VCZ curve 18 may be used as described more fully below.

In accordance with exemplary and non-limiting embodiments, there may be employed a sparse calculation of the VCZ curve 18. Examples of such a sparse calculation include, but are not limited to, a calculation of correlations between given transducer element 12 lags and a sparsely sampled VCZ curve 18. In other exemplary embodiments, echoes from groups of transducer elements 12 may be appropriately delayed and then summed together prior to a correlation computation, with or without weights applied to each element.

In addition to coherence values, the variance or standard deviation of the correlation values across the aperture of a transducer 10 can be incorporated into the image values. As the signal-to-noise ratio (SNR) of the transducer elements 12 decreases, the variance in the correlation values increases. The variance of the correlation values can be used to generate contrast in the SLSC images where expected contrast, such as when utilizing B-mode imaging, may be low or virtually nonexistent.

As described above, the width of a specified portion of a computed VCZ curve 18 can be used as a metric to provide the value at each pixel location (x,y) in a SLSC image. In alternative exemplary embodiments, other metrics can be utilized to generate SLSC image values. For example, the slope of a VCZ curve 18 from one correlation threshold to another (e.g., 1.0 to 0.4, 0.9 to 0.2, etc.) may be used. Likewise, the area under a VCZ curve 18 for a specified lag or for specific coherence coefficient thresholds $\rho_{thr}$, or the sum of the coherence coefficients $\rho$ for specified lags may be utilized.

In accordance with exemplary and non-limiting embodiments, the techniques and metric computations utilized to create SLSC images 10 can be applied to higher order arrays, such as, for example, 1.25-D, 1.5-D, 1.75-D and 2-D arrays. For these higher order arrays, the signals received by the transducer elements 12 may be summed across an elevation dimension, and the above described VCZ curve 18 and SLSC image value computations can be applied to the resulting summed transducer element 10 signals. In the case of 1.75-D and 2-D arrays, a two dimensional VCZ curve 10 can be constructed. While described with reference to delay and sum beamforming involving summation in one direction, exemplary embodiments disclosed herein are not so limited. Rather, exemplary modes of beam forming practiced in accordance with exemplary embodiments disclosed herein include any and all delay and sum beam forming that may be implemented on arbitrary and/or overlapping sub-apertures and calculations of coherence functions derived from such sub-apertures.

While described herein with reference to 2-D SLSC images, it is understood that exemplary and non-limiting embodiments may extend to the application of the teachings disclosed herein to 3-D SLSC images each comprising a three dimensional volume. In such instances, embodiments described herein with reference to pixels will be understood to apply to a volumetric, 3-D SLSC image comprised of voxels.

With specific reference to a VCZ curve 18 generated from a 2-D array, the above described computations are adapted for a surface as required. For example, metrics analogous to those described above with reference to a two dimensional VCZ curve 18 may include the volume under the surface for a specified coefficient threshold $\rho_{thr}$ or specified lag distances, the average/minimum/maximum radius of the surface at given coefficient thresholds $\rho_{thr}$, average/minimum/maximum slope of a surface between specified coefficient thresholds $\rho_{thr}$, and the like.

In accordance with exemplary and non-limiting embodiments, VCZ imaging may be combined with spatial and frequency compounding where one or more VCZ curves 18 and SLSC images are computed across different transmit and/or receive sub apertures or at different frequencies. The SLSC image from each sub aperture or frequency may then be averaged together (weighted or unweighted) to create a composite image.

In accordance with another exemplary and non-limiting embodiment, an SLSC image may be derived from synthetic aperture sequences, whereby multiple transmit and/or receive apertures are used to generate the data necessary for computation of the VCZ curve.

In accordance with yet another exemplary embodiment, an SLSC image can be derived from harmonic frequencies. In such an instance, transducer element 12 signals are bandpass filtered and/or summed with their pulse inverted counterpart to remove the fundamental component. The remaining signal is primarily made up of second harmonics. The transducer element-to-transducer element correlations are then performed on the second harmonic signals.

In accordance with yet another exemplary embodiment, a SLSC image can be created after arrival-time correction of the element 12 signals. Arrival-time correction is used to improve the spatial coherence across the aperture to compensate for wave front distortions and aberrations.

In accordance with another exemplary embodiment, a SLSC image can be used to weight (e.g., multiply or add) the B-mode echo data or to apply a "reject" threshold in which the B-mode echo value, corresponding to a pixel in a B-mode image, is set to zero or a minimum value if a metric derived from the VCZ curve 18, for the same pixel, is below a predetermined reject threshold.

In accordance with an exemplary and non-limiting embodiment, the SLSC image computed by cross-correlation computer 26 may incorporate a display upon which the SLSC image 28 may be displayed. In another embodiment, the B-mode image 24 may form an input to cross-correlation computer 26 whereat B-mode image 24 and SLSC image 28 may be combined as described above with the resulting image displayed such as upon a display of cross-correlation computer 26. In yet another embodiment, the function of ultrasound B-mode image processor 22 and cross-correlation computer 26 may be combined into a single processor.

Figure 5:
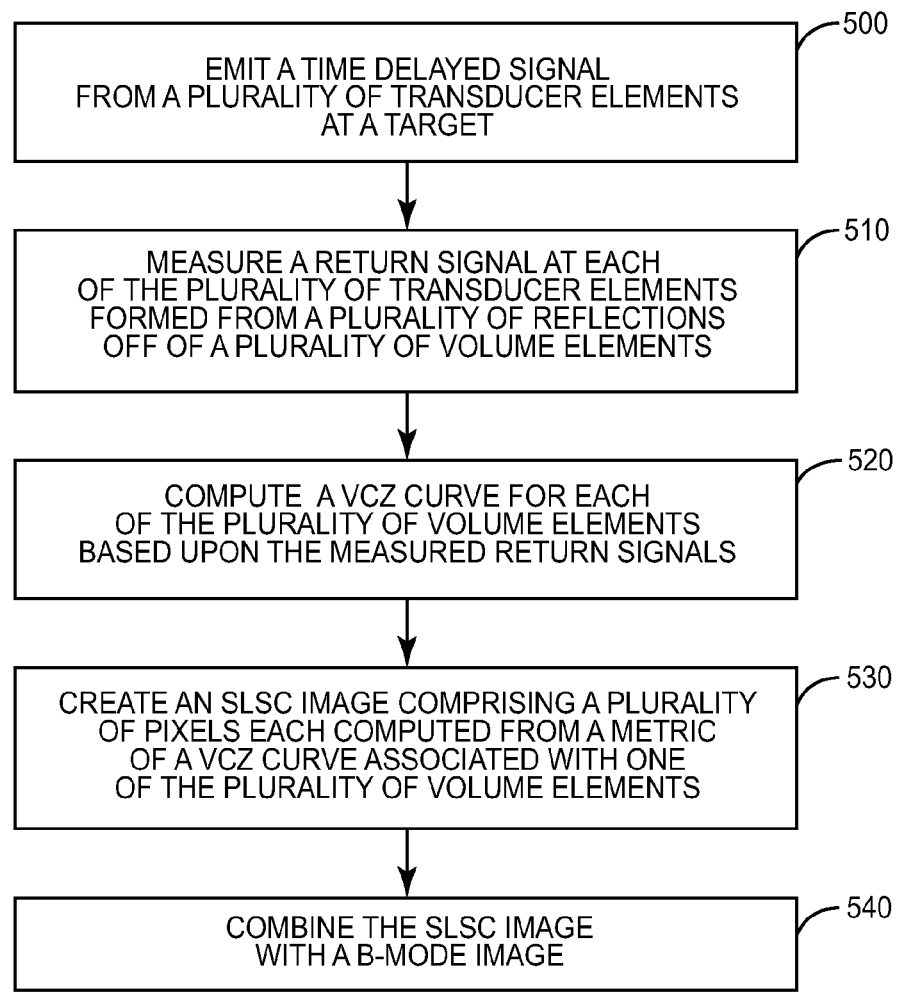
FIG. 5 illustrates a flow diagram of the of the process of VCZ imaging according to an embodiment of the present disclosure.

FIG. 5 illustrates in abbreviated form an exemplary and non-limiting embodiment flowchart for VCZ imaging a with reference to FIG. 4 described above.

In accordance with an exemplary embodiment, a time delayed signal is emitted from a plurality of transducer elements at a target (block 500). Next, a return signal is measured at each of the plurality of transducer elements formed from a plurality of reflections off of a plurality of volume elements forming a two dimensional slice of the target (block 510). A VCZ curve is then computed for each of the plurality of volume elements based upon the measured return signals (block 520) and an SLSC image is created comprising a plurality of pixels each associated with one of the plurality of volume elements wherein each of the plurality of pixels comprises a value computed from a metric of the VCZ curve computed for each of the associated plurality of volume elements (block 530). In accordance with an exemplary embodiment, SLSC image 28 may be optionally combined with B-mode image 24 (block 540).

Figure 6:
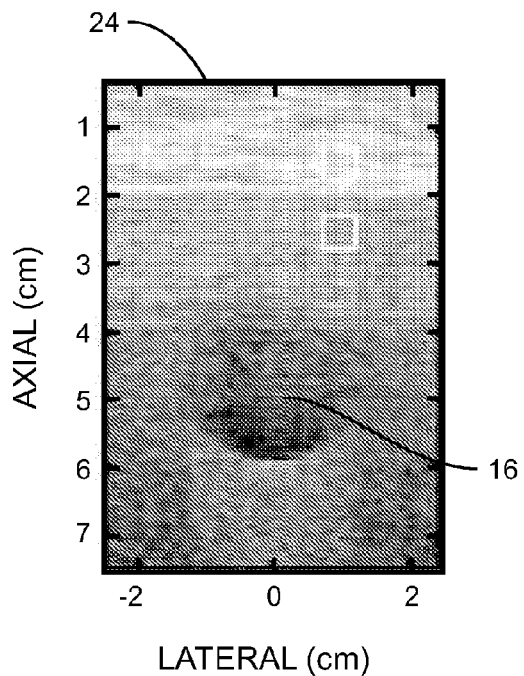
FIG. 6 is an illustration of a simulated B-mode image of a sample target.
Figure 7A:
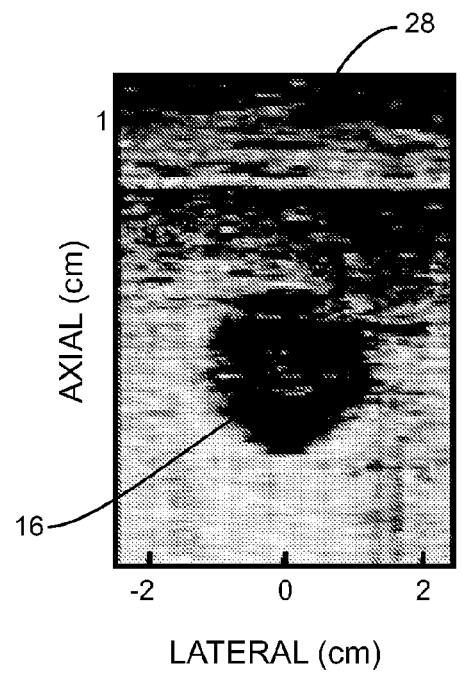
FIGS. 7A-7C are illustrations of images of the sample target of FIG. 5 each computed using a different curve metric according to exemplary embodiments disclosed herein.
Figure 7B:
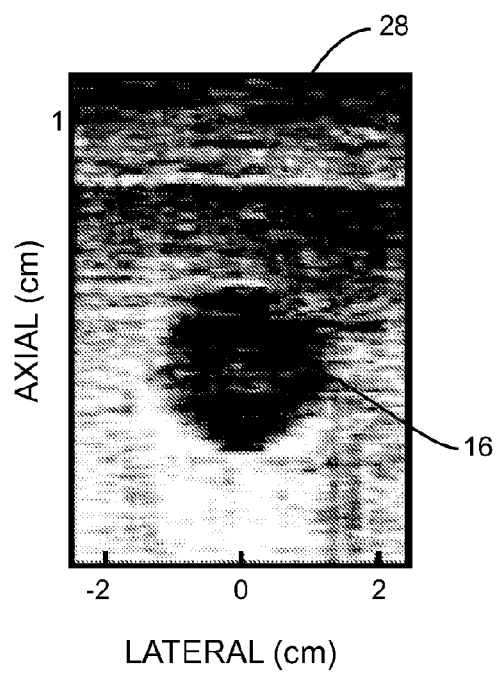
Figure 7C:
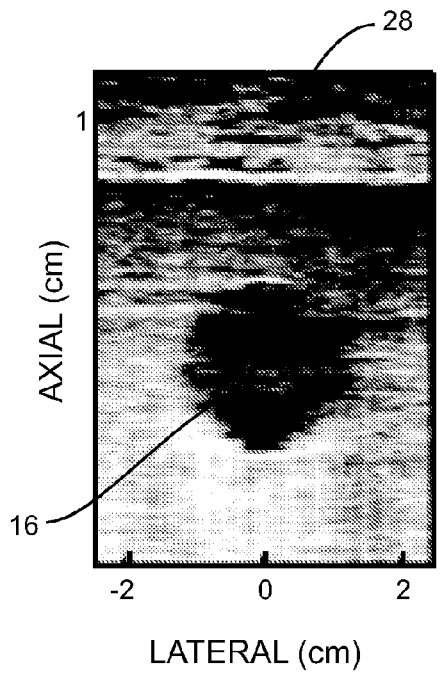

FIG. 6 is an illustration of a B-mode image 24 of a target. FIG. 7A is an illustration of an SLSC image 28 of the same target 16 as in FIG. 6 wherein a metric related to the slope of each VCZ curve is utilized. FIG. 7B is an illustration of an SLSC image 28 of the same target 16 as in FIG. 6 wherein a metric related to an integral of each VCZ curve is utilized. Specifically, a metric is derived from an integral of each VCZ such as, for example, the integral of the VCZ curve up to a predetermined value 'M', an integral of each VCZ curve for some range of lags, and the like. FIG. 7C is an illustration of an SLSC image 28 of the same target 16 as in FIG. 6 wherein a metric related to a sum of each VCZ curve is utilized.

As noted above, the spatial coherence of backscattered ultrasound waves is described by the van Cittert Zernike (VCZ) theorem, a fundamental tenet of modern optics. The theorem predicts the mutual intensity (also termed spatial covariance, mutual coherence evaluated at zero delay, or spatial coherence function) of a wave field produced by an incoherent source. According to this theorem, the spatial coherence of two points in an observation region is the scaled Fourier transform of the intensity distribution of an incoherent source. The VCZ theorem has recently been applied to pulse-echo ultrasonic imaging, where diffuse scatterers in the isochronous volume insonified by a transmit beam represent an incoherent source. At the transmit focus, the spatial covariance of backscattered echoes can be modeled as the autocorrelation of the transmit aperture. For a 1-D linear array with no apodization, the spatial covariance is equal to a triangle function with a base twice as wide as the aperture width. This theoretical model of spatial covariance has been compared to simulation and experimental results with notable agreement. There has further been utilized a k-space representation to predict spatial covariance and arrived at a similar result.

The spatial covariance of backscattered echoes is affected by several parameters, such as transmit beam shape, scatterer characteristics, receiver directivity, aberrations, gross velocity errors, and element nonuniformities. These factors scale, alter, or invalidate theoretical predictions of spatial covariance. For example, focal errors, aberrations, and element nonuniformities shorten coherence lengths. When the transmit aperture is Gaussian apodized, coherence is increased between small spatial differences and degraded at large spatial differences. Diffuse or coherent targets laterally displaced from the transmit beam will decrease coherence lengths.

The inverse Fourier transform of measured spatial coherence functions has been utilized to reconstruct transmit beam patterns. Spatial coherence has also been used to predict the performance of adaptive imaging methods. For example, there has been described a coherence-based metric to analyze signals from scattering media. This metric, called the "coherence factor", is a ratio of the coherent sum of signals across an aperture to the incoherent sum of these signals and describes focusing quality. There has been proposed an adaptive imaging technique based on a generalized version of the coherence factor. In this method, data containing high spatial frequencies are excluded from the coherent sum. The exclusion of high spatial frequencies suppresses signals from outside the main direction of the transmit beam. The generalized coherence factor (GCF) is then calculated as the ratio of the modified coherent sum to the incoherent sum. It is used to weight the beam sum prior to image formation wherein the weight functions as a multiply weight. Other exemplary embodiments utilize a phase coherence factor (PCF), which is based on the standard deviation of the phase of signals across the aperture, to weight the beam sum prior to image formation. There has been observed a direct relationship between spatial coherence and receive beamformer gain. Gain is defined as the ratio between beamformer output power and the total power of echoes at each element. It may also be represented as the weighted area under the normalized spatial coherence function.

In accordance with exemplary and non-limiting embodiments there is described below, a method for extracting useful information from coherence functions to yield images that have the potential to compete with conventional ultrasound B-mode images. Exemplary embodiments of imaging methods based on local measurements of the spatial coherence at short lags of backscattered echoes are also described. Theory and simulation results of this method under various imaging conditions are explored. Lastly, experimental phantom and clinical images based on this method are presented and compared to matched B-mode images.

For a receiving aperture with N elements of equal spacing, the signal received by the ith element is defined as $s_i(n)$, where n is the depth or time, in samples, and $s_i(n)$ is a zero-mean signal. Because pulse-echo ultrasound is broadband and applied in the near-field, the signals received across the receiving aperture must be time-delayed so that the signals at sample n correspond to the same location. After time delay of the element signals, the average, estimated spatial covariance across the receive aperture can be calculated as $$\hat{C}(m) = \frac{1}{N-m} \sum_{i=1}^{N-m} \sum_{n=n_1}^{n_2} s_i(n) s_{i+m}(n) \qquad (1)$$

where m is the distance, or lag, in number of elements between two points in the aperture. Normalizing the covariance by the variance of the signals $s_i(n)$ and $s_{i+m}(n)$, the spatial correlation can be computed by $$\hat{R}(m) = \frac{1}{N-m} \sum_{i=1}^{N-m} \frac{\sum_{n=n_1}^{n_2} s_i(n) s_{i+m}(n)}{\sqrt{\sum_{n=n_1}^{n_2} s_i^2(n) \sum_{n=n_1}^{n_2} s_{i+m}^2(n)}} \qquad (2)$$

The choice of the normalizing term differs from methods that operate to normalize Eq. 1 by the estimated spatial covariance at zero lag. However, both normalization terms serve the same purpose in that the relative strength of the echo signals are removed from the spatial coherence terms.

Figure 8:
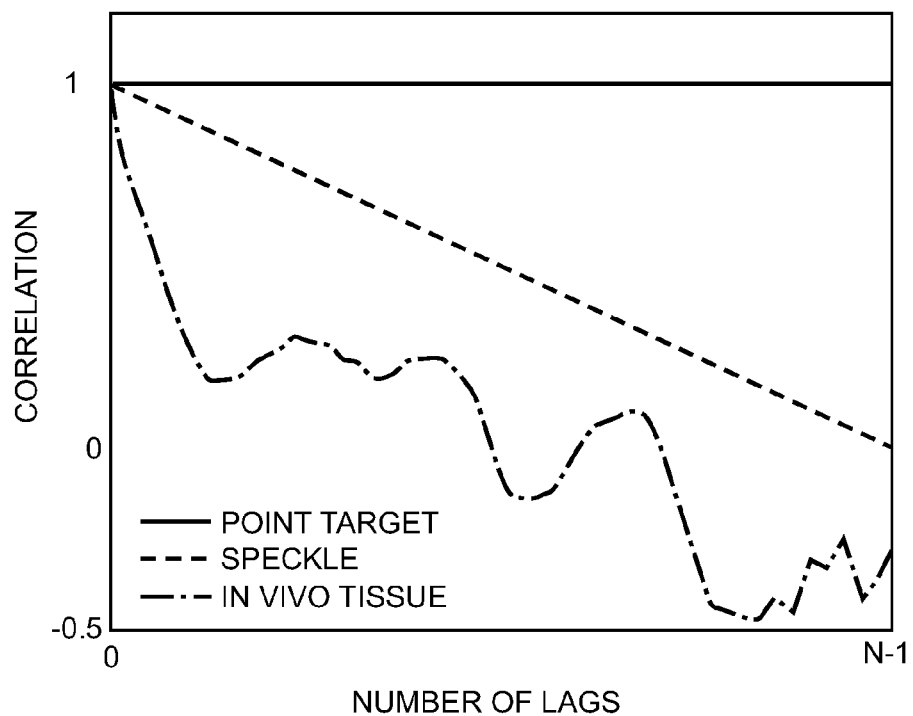
FIG. 8 is an exemplary embodiment of ideal coherence functions in a point target and speckle background, as well as an experimental coherence function from in vivo thyroid tissue.

FIG. 8 illustrates the theoretical spatial coherence across the receive aperture for a point target, uniformly distributed diffuse scatterers, and in vivo echoes from a human thyroid. In the case of a point target, the source function is modeled as an impulse, and the expected spatial coherence is constant across the aperture. For diffuse scatterers, the source function is modeled as a constant, and the source intensity distribution is modeled as a squared sinc function (arising from the lateral transmit beam shape). The corresponding expected spatial coherence is a triangle, or a line decreasing from 1 at zero-lag to 0 at lag N−1. Spatial coherence in tissue surrounding an in vivo human thyroid is expected to be similar to that of diffuse scatterers. However, the coherence demonstrated in FIG. 8 indicates that there is underlying corruption of the signals, such as strong off-axis targets and acoustic and electronic noise that decreases spatial coherence across the aperture.

For a known transmit beam, spatial coherence varies depending on the lateral backscatter distribution and the amount of signal corruption. While it is difficult to increase spatial coherence above the predicted coherence for diffuse scatterers without a strongly-reflecting and/or a laterally-compact target at the transmit focus, a decrease in spatial coherence below the expected value for diffuse targets is relatively easy to observe through increased noise or decreased on-axis source strength. In this case, the largest differences in spatial coherence are expected to occur in the regions of low lags, or in the coherence between closely separated elements. There is therefore described a metric, called the short-lag spatial coherence (SLSC), as the integral of the spatial coherence function over the first M lags:

$$R_{sl} = \int_1^M \hat{R}(m) dm \approx \sum_{m=1}^M \hat{R}(m) \quad (3)$$

M is typically in the range of 5-20 for 64-192-element transmitting arrays.

Field II [?] Received channel signals from a variety of imaging targets were modeled. Three dimensional phantoms containing a spherical lesion and three point targets were utilized, where the contrast of the lesion was varied from anechoic to 6 dB. The point target brightness in each phantom was varied from 6 to 24 dB, relative to the rms value of the diffuse scatterer strength. Each phantom measured 6 mm axially by 10 mm laterally by 10 mm in elevation and contained 20 scatterers per resolution volume. The simulated transducer was a linear array with a 5.7 MHz center frequency and 60% fractional bandwidth. The array had a lens focused at 3.75 cm in elevation, and the lateral focus was set to the same depth. An F/2 system was applied on transmit and dynamic-receive beamformer delays were applied to the channel signals. No apodization was applied to the transmit aperture. Parameters of the simulated transducer are listed in Table I.

TABLE I

SIMULATED TRANSDUCER PARAMETERS

| Parameter | Value |
|---|---|
| Number of Elements | 96 |
| Element Height | 7.5 mm |
| Element Width | 0.176 mm |
| Kerf | 0.025 mm |
| Center Frequency | 5.71 MHz |
| Sampling Frequency | 160 MHz |
| Fractional Bandwidth | 60% |

Uniform white noise, 6 dB down from the rms signal strength, was added to the channel signals to suppress coherence from low amplitude echoes. These echoes are a few orders of magnitude below backscattered and off-axis echoes and reside below the noise floor seen in ultrasonic data. Because coherence calculations do not depend on signal magnitude, these low-amplitude echoes can provide coherence estimates unlikely to be observed in experimental measurements. Introducing incoherent noise with amplitudes greater than these echoes suppresses artifacts in the simulated images and adds a degree of realism to the echo signals. To analyze the lateral resolution of coherence images, a phantom containing two regions with a 12 dB backscatter difference, separated by a vertical boundary, is used to compute a spatial step function. An estimated lateral point-spread function is then created by numerical differentiation of the step function.

The spatial covariance of wave fronts across an aperture can be predicted by the Fourier Transform of the square of the product of the lateral transmit beam pressure and the lateral backscatter, or source, function. For a lesion, the source function was modeled as a constant plus a rectangle function, with the amplitude of the rectangle equal to the contrast of the lesion and the width of the rectangle equal to the diameter of the lesion.

The spatial covariance was then numerically computed using the Fast Fourier Transform of the product of the transmitted beam amplitude times the source function, and evaluated at the spatial frequencies $k_x = x/\lambda z$, where x is the lateral spatial dimension, $\lambda$ is the wavelength, and z is the distance between the source and the aperture. The spatial covariance was then normalized at zero-lag and resampled at the spacing of the array elements. The theoretical short-lag spatial coherence was then calculated using Eq. 3. Because noise was not considered in this numerical computation, comparisons to Field II simulations were performed without noise. Note that this description of short-lag spatial coherence is valid only at the focal depth of the transmit beam. Other regions would require incorporation of the lateral intensity of the defocused transmit beam. To predict the expected short-lag spatial coherence of the Field II simulations, the transmitted intensity distribution was modeled as a squared sinc function based on the parameters in Table I.

An RMI 408 Spherical Lesion Phantom (Gammex, RMI, Middleton, Wis.) phantom containing 4 mm diameter anechoic lesions spaced 1 cm apart was imaged with a VF10-5 linear array transducer (Siemens Medical Solutions USA, Inc., Issaquah, Wash.) and a Siemens Antares™ ultrasound scanner (Siemens Medical Solutions USA, Inc.). The transmit frequency was 8.0 MHz, and the number of transmit elements was adjusted to maintain a constant F/2 transmit. Individual channel signals were acquired using the Axius Direct Diagnostic User Interface (Siemens Medical Solutions USA, Inc., Issaquah, Wash.) in conjunction with a synthetic receive aperture technique. Two sets of signals were acquired, each with a unique transmit focus of 1.5 cm or 2.5 cm. The total number of receive elements in the array was 192, however only echoes from the 64 elements centered about the transmit beam were acquired. Individual channel signals were acquired for 54 lateral locations, corresponding to 54 A-lines. Dynamic-receive beamforming delays were applied to the channel signals.

In vivo individual channel data from the thyroid of a 34-year old male volunteer were acquired in addition to phantom data. An identical setup as the RMI phantom experiments was used with a few exceptions. Individual channel signals were acquired for 48 receive elements at three foci, 0.5 cm, 1.5 cm, and 2.5 cm. At each focus, the individual channel signals corresponding to 48 A-lines were acquired.

The short-lag spatial coherence was computed for the simulated, phantom, and in vivo data using Eqs. 2 and 3 with M=5. SLSC images were formed by computing the short-lag spatial coherence at each depth n, using a correlation kernel size of one wavelength, for every A-line. B-mode images were constructed with the same individual channel data using conventional delay-and-sum methods. The contrast, contrast-to-noise ratio (CNR), and speckle signal-to-noise ratio (SNR) of lesions in B-mode and SLSC images formed from simulated and experimental data were calculated. In addition, point target conspicuity in simulated images was calculated using $$\text{Conspicuity} = \frac{S_{max} - \langle S_o \rangle}{\sigma_o} \quad (5)$$

where $S_{max}$ is the peak brightness in the point target, $\langle S_o \rangle$ is the mean brightness of the background, and $\sigma_o$ is the standard deviation of the background. All image processing and data analysis was performed in MATLAB software.

Matched B-mode and SLSC simulated images are displayed in FIG. 9. The first row shows B-mode images with lesion contrasts of anechoic, −24 dB, and −18 dB, from left to right, respectively. The second row shows B-mode images with lesion contrasts of −12 dB, −6 dB, and 6 dB, from left to right, respectively. The B-mode images show 50 dB of dynamic range. Corresponding SLSC images are shown in rows three and four with 8 dB of dynamic range. Regions indicated by the white boxes in the first image were used to calculate contrast, CNR, SNR, and point target conspicuity. Visual inspection of the SLSC images show that they are similar to the B-mode images, however there is a significant loss in visualization of the point target. The variance in the speckle region appears to be reduced as well.

In FIG. 10, Field II-simulated B-mode and SLSC images without added noise are compared to a numerical computation of the theoretical SLSC image. Six simulated B-mode and SLSC images were averaged to reduce background variance. The averaged B-mode image was normalized to the same scale as the theoretical SLSC image. There is good agreement between simulation and theoretical SLSC Images. In particular, the shapes of the slopes in the region where the lesion is located are similar. The shape is a result of correlation of low-amplitude RF signals from off-axis scattering at large angles, and only occur under noise-free conditions.

Measured contrast and CNR of the simulated lesions, as a function of lesion contrast, is displayed in FIGS. 11A and 11B. Contrasts in B-mode images have excellent agreement with ideal values, whereas contrast is lost in the SLSC images. The CNR, however, increased significantly compared to the B-mode images. This is a result of the significant increase in the SNR of the images. The average speckle SNR at the focal depth in the B-mode and SLSC images is 2.1±0.3 and 17.1±3.4, respectively. Point target conspicuity as a function of point target brightness is displayed in FIG. 12. Conspicuity increases with target brightness in the B-mode images, but remains flat and significantly lower in the SLSC images.

Coherence functions generated from the simulated channel data at the focal depth are shown in FIG. 13. These coherence functions are averaged over the ROIs (indicated in FIG. 8) inside and outside the lesions. Coherence functions for the anechoic lesion and point target is shown in FIG. 13A. The variance in the correlation coefficient increases as the correlation coefficient decreases. In addition, the coherence in the anechoic region rapidly decreases in the first few lags. This indicates that the most useful information needed to distinguish tissue regions can be obtained in the short-lag (M=5-20) region. FIG. 13B demonstrates similar coherence functions for the −12 dB lesion.

FIG. 14 shows the contrast of the anechoic lesion and speckle SNR of the SLSC and B-mode images as a function of M. In this figure, M refers to the number of lags (Eq. 3) in the SLSC image, and number of receive aperture elements in the B-mode image. In FIG. 14A, the contrast in the SLSC image is optimal for M ranging from 16 to 20. The contrast in the B-mode images improves with increasing number of receive elements and is optimal at the maximum number of receive elements. Predictably, the speckle SNR in the SLSC images decreases with increasing M, but is up to an order of magnitude higher than that of B-mode images. The lateral resolution of the SLSC images was determined to be 0.45, 0.86, and 1.40 mm at −6, −10, and −20 dB, respectively, using numerical differentiation. The resolution of the matched B-mode images was 0.43, 0.55, and 0.74 mm at −6, −10, and −20 dB, respectively. The numerical differentiation technique underestimated resolution, when compared to values obtained with more conventional techniques. From the autocorrelation of speckle, the B-mode images were determined to have a resolution of 0.50, 0.64, and 0.88 mm at −6, −10, and −20 dB, respectively. The theoretical estimation of $\lambda z/D$ for lateral resolution is determined to be 0.54 mm at −6 dB and compares favorably with the autocorrelation of speckle.

The axial resolution of the coherence images is approximately equal to the kernel length convolved with half the pulse length, as in correlation-based imaging techniques such as ARFI and elastography. In all coherence images, the correlation kernel length was approximately $\lambda$.

Matched B-mode and SLSC images of the RMI spherical lesion phantom are shown in FIG. 15. M was set to 5, 10, and 15 for the three SLSC images to demonstrate changes in image characteristics with increasing M. The SLSC images show a limited depth of field about the focal depth, compared to the B-mode images. The effect is more pronounced with increasing M. In addition, the lesion boundaries appear increasingly blurred with decreasing M, an indication of loss of resolution.

Contrast and CNR of the lesion at the focus and speckle SNR at the focus of B-mode and SLSC images are reported in Table II. The differences in contrast are marginal for the three SLSC images, but CNR and SNR decrease with increasing M.

In vivo B-mode, SLSC, and spatially compounded images of a human thyroid are shown in FIG. 16. The images were blended from data acquired at three transmit foci to create a uniform image. The SLSC image was created using M=5, and the spatially-compounded image was created from 43 B-mode images with 5-element receive apertures spaced 1-element apart. A cyst is visible in the thyroid at 1.5 cm depth.

Contrast and CNR of the cyst and speckle SNR at 1.5 cm are reported in Table II.

TABLE II

CONTRAST, CNR, AND SNR AT FOCUS OF EXPERIMENTAL PHANTOM, SIMULATED, AND IN VIVO THYROID DATA.

|  | Contrast (dB) | CNR | SNR |
| --- | --- | --- | --- |
| Experimental phantom images | | | |
| B-mode | −17.3 | 1.6 | 1.7 |
| SLSC, M = 5 | −13.6 | 16.2 | 15.8 |
| SLSC, M = 10 | −14.3 | 10.1 | 9.0 |
| SLSC, M = 15 | −14.3 | 7.4 | 6.2 |
| In vivo thyroid images | | | |
| B-mode | −20.3 | 1.9 | 2.1 |
| SLSC | −37.7 | 5.3 | 5.8 |
| Spatial-compounded | −14.4 | 2.8 | 3.5 |

Contrast is improved by 17 dB in the SLSC image compared to the B-mode image. Contrast in the spatially-compounded image is reduced by −6 dB compared to the B-mode image.

As suggested by FIG. 13, the first few lags of the spatial coherence function contain high CNR information allowing discrimination of diffuse scatterer regions. Generally, diffuse scatters have higher spatial coherence than anechoic or hypoechoic regions at these short lags. Utilizing the coherence information of these short lags, as opposed to all lags in the coherence function, images with higher CNR in hypoechoic and anechoic regions and higher SNR compared to B-mode images are created.

There are several notable features of SLSC imaging. First, the effective SNR for regions of diffuse scatterers is markedly higher in SLSC images compared to B-mode images. This is due to a reduced variance of the signal attributed to diffuse scattering regions. Second, due to the lack of receive beamforming in the SLSC images, the resolution is primarily determined by the transmit beam shape. Therefore, the resolution of the SLSC image is significantly worse than the corresponding B-mode image. However, as indicated in FIG. 15, the resolution can be improved by increasing M. The improved resolution is due to the addition of higher spatial frequency content from the larger lags of the receive beamformer. Lastly, while contrast may be reduced in the SLSC image, the CNR of hypoechoic targets is increased. SLSC imaging may be useful in cardiac and fetal imaging applications where high contrast borders, potentially obscured by clutter, are present.

As demonstrated in FIG. 15, the most useful information in SLSC images is contained within the depth of field of the transmit beam. This challenge can be overcome by blending multiple foci at the cost of frame rate, as is often employed in B-mode imaging, or by using synthetic transmit aperture. Spatial compounding is a favored method for reducing speckle variance in ultrasound images. The spatially-compounded coherence image in FIG. 16C compares the averaging of equivalent-sized receive apertures to SLSC imaging lag. Using the same data, the improvement in speckle SNR is tripled for the SLSC image and only doubled in the spatial compounding image. In addition, the apparent detail of the cyst is worse in the spatial compounding image compared to the SLSC image.

The GCF and PCF coherence metrics were used to weight B-mode data. The SLSC measurement can also be used to weight B-mode images. In this case, speckle will be present in the weighted image, but acoustic noise will often be reduced.

Characteristics of ultrasound spatial coherence may be used to reconstruct images having the potential to compete with conventional B-mode images. This method has been demonstrated with simulated and experimental data. Coherence images calculated with normalized cross correlation have enhanced signal-to-noise and contrast-to-noise ratios. The limited depth of field in coherence images may be overcome by adjoining images acquired at different transmit foci.

The cross-correlation computer 26 according to embodiments disclosed herein may be provided in or integrated into any processor-based device for controlling access to memory. Examples, without limitation, include a computer, a portable computer, a desktop computer, a personal digital assistant (PDA), a monitor, a computer monitor and the like.

In this regard, FIG. 17 illustrates an example of a cross-correlation computer 26. In this example, cross-correlation computer 26 includes one or more central processing units (CPUs) 32 each including one or more processors 34. CPU(s) 32 may be a master device. The CPU(s) 32 may have cache memory 36 coupled to the processor(s) 34 for rapid access to temporarily stored data. CPU(s) 32 is coupled to system bus 38, which intercouples other devices included in cross-correlation computer 26. As is well known, CPU(s) 32 communicates with other devices by exchanging address, control, and data information over system bus 38. For example, CPU(s) 32 can communicate memory access requests to external memory via communications to the memory controller 40 as a slave device.

Other master and slave devices can be connected to the system bus 38. Such devices can include one or more input devices 42, one or more output devices 44, one or more network interface devices 46, and one or more display controllers 48, as examples. Input device(s) 42 can include any type of input device, including but not limited to input keys, switches, voice processors, etc. Output device(s) 46 can include any type of output device, including but not limited to audio, video, other visual indicators, etc. Network interface device(s) 46 can be any devices configured to allow exchange of data to and from network 50. Network 50 can be any type of network, including but not limited to a wired or wireless network, private or public network, a local area network (LAN), a wide local area network (WLAN), and the Internet. Network interface device(s) 46 can be configured to support any type of communication protocol desired.

CPU 32 may also be configured to access the display controller(s) 48 over system bus 38 to control information sent to one or more displays 52. Display controller(s) 48 sends information to the display(s) 52 to be displayed via one or more video processors 54, which process the information to be displayed into a format suitable for display(s) 52. Display(s) 52 can include any type of display, including but not limited to a cathode ray tube (CRT), a liquid crystal display (LCD), a plasma display, etc.

Memory controller 40 may communicate with one or more drives 56 comprising at least one computer readable medium 58 on which may be stored instructions 60, such as instructions incorporated in software, adapted to direct the functioning of cross-correlation computer 26 in accordance with the exemplary embodiments described above.

Those of skill in the art would further appreciate that the various illustrative logical blocks, modules, circuits, and algorithms described in connection with the embodiments disclosed herein may be implemented as electronic hardware, instructions stored in memory or in another computer-readable medium and executed by a processor or other processing device, or combinations of both. The memory controllers, arbiter, master devices, and sub-master devices described herein may be employed in any circuit, hardware component, integrated circuit (IC), or IC chip, as examples. The memory may be any type and size of memory and may be configured to store any type of information desired. To clearly illustrate this interchangeability, various illustrative components, blocks, modules, circuits, and steps have been described above generally in terms of their functionality. How such functionality is implemented depends upon the particular application, design choices, and/or design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a processor, a DSP, an Application Specific Integrated Circuit (ASIC), a FPGA or other programmable logic device, discrete gate or transistor logic, discrete hardware components, or any combination thereof designed to perform the functions described herein. A processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The embodiments disclosed herein may be embodied in hardware and in instructions that are stored in hardware, and may reside, for example, in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of computer readable medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a remote station. In the alternative, the processor and the storage medium may reside as discrete components in a remote station, base station, or server.

It is also noted that the operational steps described in any of the exemplary embodiments herein are described to provide examples and discussion. The operations described may be performed in numerous different sequences other than the illustrated sequences. Furthermore, operations described in a single operational step may actually be performed in a number of different steps. Additionally, one or more operational steps discussed in the exemplary embodiments may be combined. It is to be understood that the operational steps illustrated in the flow chart diagrams may be subject to numerous different modifications as will be readily apparent to one of skill in the art. Those of skill in the art would also understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

While described in herein and illustrated in exemplary manner with reference to various tissue types, the present disclosure is not so limited. Rather, the teachings of the present disclosure extend to and include, without limitation, any and all types of organic and inorganic materials, including all forms of tissue, human or otherwise, that may be ultrasonically imaged.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but is to be accorded the widest scope consistent with the principles and novel features disclosed herein.

What is claimed is:

1. A method of creating an ultrasound image comprising:
receiving a return signal from a time delayed signal emitted from a plurality of transducer elements at a target, wherein the return signal comprising a measurement at each of the plurality of transducer elements formed from a plurality of reflections off of a plurality of volume elements forming a two dimensional slice of a target;
computing a Van-Cittert Zernike (VCZ) curve for each of the plurality of volume elements based upon the measured return signals; and
creating a short-lag spatial coherence (SLSC) image, the SLSC image being an image based on at least one metric derived from at least a portion of the computed VCZ curves for the plurality of volume elements,
the SLSC image comprising a plurality of pixels, wherein each of the plurality of pixels is associated with one of the plurality of volume elements, and wherein each of the plurality of pixels comprises a value computed from the at least one metric derived from the at least one portion of the respective VCZ curve computed for the volume element associated with the pixel.

2. The method of claim 1, wherein the at least one metric comprises a slope of the VCZ curve.

3. The method of claim 2, wherein the slope extends from a predefined first threshold to a predefined second threshold.

4. The method of claim 1, wherein the at least one metric comprises a distance from an origin of the VCZ curve to a point on an x-axis of the VCZ curve where a value of the VCZ curve is equal to a predefined threshold.

5. The method of claim 4, wherein the at least one metric comprises an integral of the VCZ curve over the distance from the origin of the VCZ curve to the point on an x-axis of the VCZ curve where of the VCZ curve is equal to a predefined threshold.

6. The method of claim 1, wherein the at least one metric comprises a sum of correlation coefficients for the VCZ curve.

7. The method of claim 1, wherein the at least one metric comprises an integral of the VCZ curve between two predefined thresholds on the y-axis of the VCZ curve.

8. The method of claim 1, wherein the plurality of transducer elements form a higher order array.

9. The method of claim 8, wherein the higher order array is selected from the group consisting of a 1.25-D array, a 1.5-D array, a 1.75-D array and a 2-D array.

10. The method of claim 9 wherein, for the 2-D array, the at least one metric is selected from the group consisting of a volume under a surface for a predefined coefficient threshold and a volume under a surface for a predefined lag distance.

11. The method of claim 9 wherein, for the 2-D array, the at least one metric is selected from the group consisting of an average radius, a minimum radius and a maximum radius of a surface at a predefined coefficient threshold.

12. The method of claim 9 wherein, the 2-D array, the at least one metric is selected from the group consisting of an average slope, a minimum slope and a maximum slope of a surface between a first predefined coefficient threshold and a second predefined coefficient threshold.

13. The method of claim 1, further comprising: computing at least one additional VCZ curve for each of the plurality of volume elements based upon the measured return signals; and
creating at least one additional SLSC image based on the at least one metric derived from the at least a portion of the additional computed VCZ curves for the plurality of volume elements
the additional SLSC image comprising a plurality of pixels each associated with one of the plurality of volume elements, wherein each of the plurality of pixels comprises a value computed from the at least one metric derived from the at least one portion of the respective at least one additional VCZ curve computed for the volume element associated with the pixel; and
creating a composite image from the SLSC image and the at least one additional SLSC image.

14. The method of claim 13, wherein each VCZ curve is associated with a subset of the plurality of transducer elements forming a sub aperture, each at least one additional VCZ curve is associated with a subset of the plurality of transducer elements forming a sub aperture and wherein the sub apertures associated with the VCZ curves differ from the sub apertures associated with the at least one additional VCZ curve.

15. The method of claim 13, wherein the SLSC image comprises a corresponding first frequency and the at least one additional SLSC image comprises a second frequency wherein the first frequency differs from the second frequency.

16. The method of claim 1, further comprising, prior to creating the SLSC image, applying arrival-time correction to the return signal.

17. The method of claim 1, further comprising combining the SLSC image with a B-mode image to produce a combined image.

18. The method of claim 17, wherein a value of at least one of the plurality of pixels comprising the SLSC image is a reject threshold.

19. The method of claim 18, wherein combining the SLSC image with the B-mode image comprises assigning a pixel value for each pixel in the B-mode image to a corresponding pixel in the combined image if the corresponding pixel in the SLSC image is equal to or greater than the reject threshold, else assigning a pixel for each pixel in the B-mode image comprising a minimum value.

20. The method of claim 19, wherein the minimum value is zero.

21. The method of claim 1, further comprising, prior to creating the SLSC image, applying harmonic imaging to the return signal.

22. A non-transitory computer-readable medium, comprising instructions for instructing a computer to:
  receive a return signal from a time delayed signal emitted from a plurality of transducer elements at a target the return signal comprising a measurement at each of the plurality of transducer elements formed from a plurality of reflections off of a plurality of volume elements forming a two dimensional slice of a target;
  compute a Van-Cittert Zernike (VCZ) curve for each of the plurality of volume elements based upon the measured return signals; and
  create a short-lag spatial coherence (SLSC) image, the SLSC image being an image based on at least one metric derived from at least a portion of the computed VCZ curves for the plurality of volume elements,
  the SLSC image comprising a plurality of pixels, wherein each of the plurality of pixels is associated with one of the plurality of volume elements, and wherein each of the plurality of pixels comprises a value computed from the at least one metric derived from the at least one portion of the respective VCZ curve computed for the volume element associated with the pixel.

* * * * *